(12) United States Patent
Gandhi

(10) Patent No.: US 11,695,050 B2
(45) Date of Patent: Jul. 4, 2023

(54) ASSEMBLIES WHICH INCLUDE RUTHENIUM-CONTAINING CONDUCTIVE GATES

(71) Applicant: Micron Technology, Inc., Boise, ID (US)

(72) Inventor: Ramanathan Gandhi, Singapore (SG)

(73) Assignee: Micron Technology, Inc., Boise, ID (US)

( * ) Notice: Subject to any disclaimer, the term of this patent is extended or adjusted under 35 U.S.C. 154(b) by 7 days.

(21) Appl. No.: 17/194,971

(22) Filed: Mar. 8, 2021

(65) Prior Publication Data

US 2021/0217863 A1 Jul. 15, 2021

Related U.S. Application Data

(62) Division of application No. 16/383,964, filed on Apr. 15, 2019, now Pat. No. 10,964,793.

(51) Int. Cl.
*H01L 21/28* (2006.01)
*H01L 29/66* (2006.01)
(Continued)

(52) U.S. Cl.
CPC ...... *H01L 29/4234* (2013.01); *H01L 29/4958* (2013.01); *H10B 43/10* (2023.02); *H10B 43/27* (2023.02)

(58) Field of Classification Search
CPC .......... H01L 29/4234; H01L 27/11582; H01L 27/11565; H01L 29/4958; H01L 27/11519;
(Continued)

(56) References Cited

U.S. PATENT DOCUMENTS 8,258,034 B2 9/2012 Ramaswamy et al.
9,711,530 B1 7/2017 Ikawa et al.
(Continued)

FOREIGN PATENT DOCUMENTS

EP 20790832 12/2022
JP 2013-187421 9/2013
(Continued)

OTHER PUBLICATIONS

Breuil et al., "Optimization of Ru based Hybrid Floating Gate for Planar NAND Flash", 2015, IEEE International Memory Workshop (IMW), 4 pages.

*Primary Examiner* — Shahed Ahmed
*Assistant Examiner* — Khatib A Rahman
(74) *Attorney, Agent, or Firm* — Wells St. John P.S.

(57) ABSTRACT

Some embodiments include a memory cell having a conductive gate comprising ruthenium. A charge-blocking region is adjacent the conductive gate, a charge-storage region is adjacent the charge-blocking region, a tunneling material is adjacent the charge-storage region, and a channel material is adjacent the tunneling material. Some embodiments include an assembly having a vertical stack of alternating insulative levels and wordline levels. The wordline levels contain conductive wordline material which includes ruthenium. Semiconductor material extends through the stack as a channel structure. Charge-storage regions are between the conductive wordline material and the channel structure. Charge-blocking regions are between the charge-storage regions and the conductive wordline material. Some embodiments include methods of forming integrated assemblies.

28 Claims, 21 Drawing Sheets

(51) Int. Cl.
*H01L 29/423* (2006.01)
*H01L 29/49* (2006.01)
*H10B 43/10* (2023.01)
*H10B 43/27* (2023.01)

(58) Field of Classification Search
CPC ........... H01L 27/11556; H01L 27/1157; H01L 27/11573; H01L 29/66833; H01L 29/792; H01L 29/40117; H10B 43/10; H10B 43/27; H10B 41/10; H10B 41/27; H10B 43/40; H10B 43/35
See application file for complete search history.

(56) References Cited

U.S. PATENT DOCUMENTS

| | | | |
|---|---|---|---|
| 9,812,463 | B2 | 11/2017 | Sharangpani et al. |
| 9,905,573 | B1 | 2/2018 | Mada |
| 9,972,640 | B1 * | 5/2018 | Kai ................... H01L 21/76877 |
| 2011/0303968 | A1 | 12/2011 | Lue |
| 2012/0256247 | A1 * | 10/2012 | Alsmeier ............... H10B 41/27 257/E21.422 |
| 2013/0234222 | A1 | 9/2013 | Yasuda et al. |
| 2015/0179662 | A1 | 6/2015 | Makala et al. |
| 2015/0263014 | A1 | 9/2015 | Toyonaga |
| 2016/0043100 | A1 * | 2/2016 | Lee ................... H01L 27/11582 257/324 |
| 2016/0071861 | A1 * | 3/2016 | Serov ............... H01L 29/66825 438/257 |
| 2016/0149002 | A1 | 5/2016 | Sharangpani et al. |
| 2016/0149049 | A1 * | 5/2016 | Sharangpani ..... H01L 27/11548 257/314 |
| 2016/0343729 | A1 * | 11/2016 | Shin .................. H01L 29/40114 |
| 2017/0025431 | A1 | 1/2017 | Kanakamedala et al. |
| 2018/0090373 | A1 | 3/2018 | Sharangpani |
| 2018/0097009 | A1 | 4/2018 | Zhang et al. |
| 2018/0350831 | A1 * | 12/2018 | Kim ................... H01L 27/11565 |
| 2020/0006358 | A1 | 1/2020 | Nishikawa |
| 2020/0098773 | A1 | 3/2020 | Kaneko |
| 2020/0227727 | A1 | 7/2020 | Li |

FOREIGN PATENT DOCUMENTS

| | | |
|---|---|---|
| JP | 2019-510362 | 4/2019 |
| WO | WO 2017/165027 | 9/2017 |
| WO | WO 2018/136730 | 7/2018 |
| WO | PCT/US2020/019833 | 2/2020 |
| WO | PCT/US2020/019833 | 9/2021 |

* cited by examiner

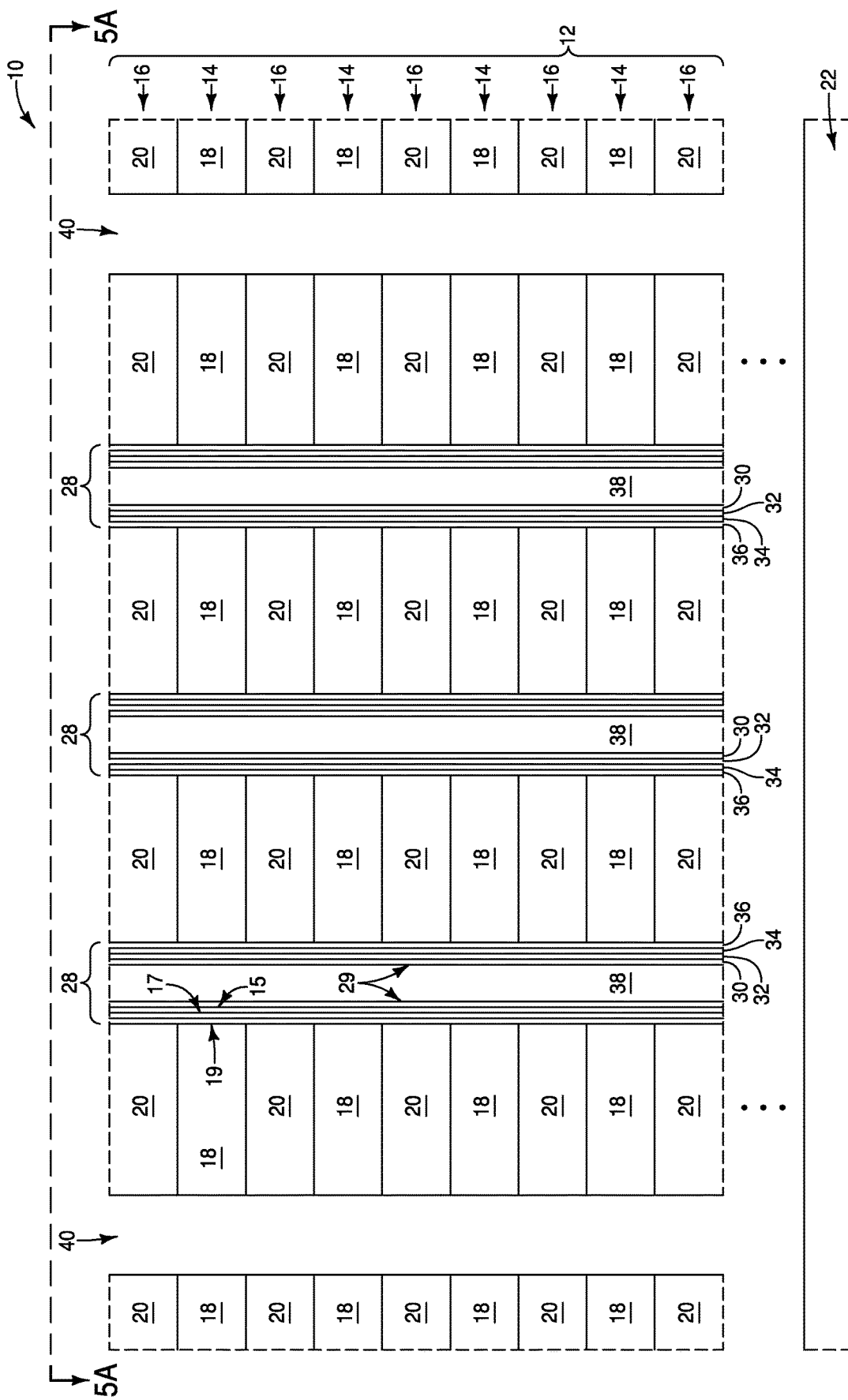

ASSEMBLIES WHICH INCLUDE RUTHENIUM-CONTAINING CONDUCTIVE GATES

RELATED PATENT DATA

This patent resulted from a divisional application of U.S. patent application Ser. No. 16/383,964, filed Apr. 15, 2019, entitled "Assemblies Which Include Ruthenium-Containing Conductive Gates", naming Ramanathan Gandhi as inventor, the disclosure of which is incorporated by reference.

TECHNICAL FIELD

Assemblies (e.g., NAND memory architectures) which include ruthenium-containing conductive gates.

BACKGROUND

Memory provides data storage for electronic systems. Flash memory is one type of memory, and has numerous uses in modern computers and devices. For instance, modern personal computers may have BIOS stored on a flash memory chip. As another example, it is becoming increasingly common for computers and other devices to utilize flash memory in solid state drives to replace conventional hard drives. As yet another example, flash memory is popular in wireless electronic devices because it enables manufacturers to support new communication protocols as they become standardized, and to provide the ability to remotely upgrade the devices for enhanced features.

NAND may be a basic architecture of flash memory, and may be configured to comprise vertically-stacked memory cells.

Before describing NAND specifically, it may be helpful to more generally describe the relationship of a memory array within an integrated arrangement. FIG. 1 shows a block diagram of a prior art device 1000 which includes a memory array 1002 having a plurality of memory cells 1003 arranged in rows and columns along with access lines 1004 (e.g., wordlines to conduct signals WL0 through WLm) and first data lines 1006 (e.g., bitlines to conduct signals BL0 through BLn). Access lines 1004 and first data lines 1006 may be used to transfer information to and from the memory cells 1003. A row decoder 1007 and a column decoder 1008 decode address signals A0 through AX on address lines 1009 to determine which ones of the memory cells 1003 are to be accessed. A sense amplifier circuit 1015 operates to determine the values of information read from the memory cells 1003. An I/O circuit 1017 transfers values of information between the memory array 1002 and input/output (I/O) lines 1005. Signals DQ0 through DQN on the I/O lines 1005 can represent values of information read from or to be written into the memory cells 1003. Other devices can communicate with the device 1000 through the I/O lines 1005, the address lines 1009, or the control lines 1020. A memory control unit 1018 is used to control memory operations to be performed on the memory cells 1003, and utilizes signals on the control lines 1020. The device 1000 can receive supply voltage signals Vcc and Vss on a first supply line 1030 and a second supply line 1032, respectively. The device 1000 includes a select circuit 1040 and an input/output (I/O) circuit 1017. The select circuit 1040 can respond, via the I/O circuit 1017, to signals CSEL1 through CSELn to select signals on the first data lines 1006 and the second data lines 1013 that can represent the values of information to be read from or to be programmed into the memory cells 1003. The column decoder 1008 can selectively activate the CSEL1 through CSELn signals based on the A0 through AX address signals on the address lines 1009. The select circuit 1040 can select the signals on the first data lines 1006 and the second data lines 1013 to provide communication between the memory array 1002 and the I/O circuit 1017 during read and programming operations.

The memory array 1002 of FIG. 1 may be a NAND memory array, and FIG. 2 shows a block diagram of a three-dimensional NAND memory device 200 which may be utilized for the memory array 1002 of FIG. 1. The device 200 comprises a plurality of strings of charge-storage devices. In a first direction (Z-Z'), each string of charge-storage devices may comprise, for example, thirty-two charge-storage devices stacked over one another with each charge-storage device corresponding to one of, for example, thirty-two tiers (e.g., Tier0-Tier31). The charge-storage devices of a respective string may share a common channel region, such as one formed in a respective pillar of semiconductor material (e.g., polysilicon) about which the string of charge-storage devices is formed. In a second direction (X-X'), each first group of, for example, sixteen first groups of the plurality of strings may comprise, for example, eight strings sharing a plurality (e.g., thirty-two) of access lines (i.e., "global control gate (CG) lines", also known as wordlines, WLs). Each of the access lines may couple the charge-storage devices within a tier. The charge-storage devices coupled by the same access line (and thus corresponding to the same tier) may be logically grouped into, for example, two pages, such as P0/P32, P1/P33, P2/P34 and so on, when each charge-storage device comprises a cell capable of storing two bits of information. In a third direction (Y-Y'), each second group of, for example, eight second groups of the plurality of strings, may comprise sixteen strings coupled by a corresponding one of eight data lines. The size of a memory block may comprise 1,024 pages and total about 16 MB (e.g., 16 WLs×32 tiers_×2 bits=1,024 pages/block, block size=1,024 pages×16 KB/page=16 MB). The number of the strings, tiers, access lines, data lines, first groups, second groups and/or pages may be greater or smaller than those shown in FIG. 2.

FIG. 3 shows a cross-sectional view of a memory block 300 of the 3D NAND memory device 200 of FIG. 2 in an X-X' direction, including fifteen strings of charge-storage devices in one of the sixteen first groups of strings described with respect to FIG. 2. The plurality of strings of the memory block 300 may be grouped into a plurality of subsets 310, 320, 330 (e.g., tile columns), such as tile column$_I$, tile column$_J$ and tile column$_K$, with each subset (e.g., tile column) comprising a "partial block" of the memory block 300. A global drain-side select gate (SGD) line 340 may be coupled to the SGDs of the plurality of strings. For example, the global SGD line 340 may be coupled to a plurality (e.g., three) of sub-SGD lines 342, 344, 346 with each sub-SGD line corresponding to a respective subset (e.g., tile column), via a corresponding one of a plurality (e.g., three) of sub-SGD drivers 332, 334, 336. Each of the sub-SGD drivers 332, 334, 336 may concurrently couple or cut off the SGDs of the strings of a corresponding partial block (e.g., tile column) independently of those of other partial blocks. A global source-side select gate (SGS) line 360 may be coupled to the SGSs of the plurality of strings. For example, the global SGS line 360 may be coupled to a plurality of sub-SGS lines 362, 364, 366 with each sub-SGS line corresponding to the respective subset (e.g., tile column), via a corresponding one of a plurality of sub-SGS drivers 322, 324, 326. Each of the sub-SGS drivers 322, 324, 326 may concurrently couple or cut off the SGSs of the strings of a corresponding partial block (e.g., tile column) independently of those of other partial blocks. A global access line (e.g., a global CG line) 350 may couple the charge-storage devices corresponding to the respective tier of each of the plurality of strings. Each global CG line (e.g., the global CG line 350) may be coupled to a plurality of sub-access lines (e.g., sub-CG lines) 352, 354, 356 via a corresponding one of a plurality of sub-string drivers 312, 314 and 316. Each of the sub-string drivers may concurrently couple or cut off the charge-storage devices corresponding to the respective partial block and/or tier independently of those of other partial blocks and/or other tiers. The charge-storage devices corresponding to the respective subset (e.g., partial block) and the respective tier may comprise a "partial tier" (e.g., a single "tile") of charge-storage devices. The strings corresponding to the respective subset (e.g., partial block) may be coupled to a corresponding one of sub-sources 372, 374 and 376 (e.g., "tile source") with each sub-source being coupled to a respective power source.

The NAND memory device 200 is alternatively described with reference to a schematic illustration of FIG. 4.

The memory array 200 includes wordlines $202_1$ to $202_N$, and bitlines $228_1$ to $228_M$.

The memory array 200 also includes NAND strings $206_1$ to $206_M$. Each NAND string includes charge-storage transistors $208_1$ to $208_N$. The charge-storage transistors may use floating gate material (e.g., polysilicon) to store charge, or may use charge-trapping material (such as, for example, silicon nitride, metallic nanodots, etc.) to store charge.

The charge-storage transistors 208 are located at intersections of wordlines 202 and strings 206. The charge-storage transistors 208 represent non-volatile memory cells for storage of data. The charge-storage transistors 208 of each NAND string 206 are connected in series source-to-drain between a source-select device (e.g., source-side select gate, SGS) 210 and a drain-select device (e.g., drain-side select gate, SGD) 212. Each source-select device 210 is located at an intersection of a string 206 and a source-select line 214, while each drain-select device 212 is located at an intersection of a string 206 and a drain-select line 215. The select devices 210 and 212 may be any suitable access devices, and are generically illustrated with boxes in FIG. 4.

A source of each source-select device 210 is connected to a common source line 216. The drain of each source-select device 210 is connected to the source of the first charge-storage transistor 208 of the corresponding NAND string 206. For example, the drain of source-select device $210_1$ is connected to the source of charge-storage transistor $208_1$ of the corresponding NAND string $206_1$. The source-select devices 210 are connected to source-select line 214.

The drain of each drain-select device 212 is connected to a bitline (i.e., digit line) 228 at a drain contact. For example, the drain of drain-select device $212_1$ is connected to the bitline $228_1$. The source of each drain-select device 212 is connected to the drain of the last charge-storage transistor 208 of the corresponding NAND string 206. For example, the source of drain-select device $212_1$ is connected to the drain of charge-storage transistor $208_N$ of the corresponding NAND string $206_1$.

The charge-storage transistors 208 include a source 230, a drain 232, a charge-storage region 234, and a control gate 236. The charge-storage transistors 208 have their control gates 236 coupled to a wordline 202. A column of the charge-storage transistors 208 are those transistors within a NAND string 206 coupled to a given bitline 228. A row of the charge-storage transistors 208 are those transistors commonly coupled to a given wordline 202.

Three-dimensional NAND architectures may have multiple vertically-stacked wordlines. In some applications, each of the wordlines may comprise a conductive liner surrounding a metal-containing core material. The conductive liner may have any of numerous purposes; and may, for example, improve adhesion of the core material, provide desired workfunction properties, etc. There is a continuing goal to increasing the number of stacked memory cells within three-dimensional NAND, and a corresponding goal to increase the number of vertically-stacked wordlines within a NAND memory array.

It would be desirable to develop improved materials suitable for utilization in three-dimensional NAND, and to develop improved methods of forming three-dimensional NAND.

BRIEF DESCRIPTION OF THE DRAWINGS

FIGS. 5-12 are diagrammatic cross-sectional side views of a region of an integrated assembly at example process stages of an example method for forming an example memory array. FIG. 5 is along the line 5-5 of FIG. 5A.

DETAILED DESCRIPTION OF THE ILLUSTRATED EMBODIMENTS

Figure 1:
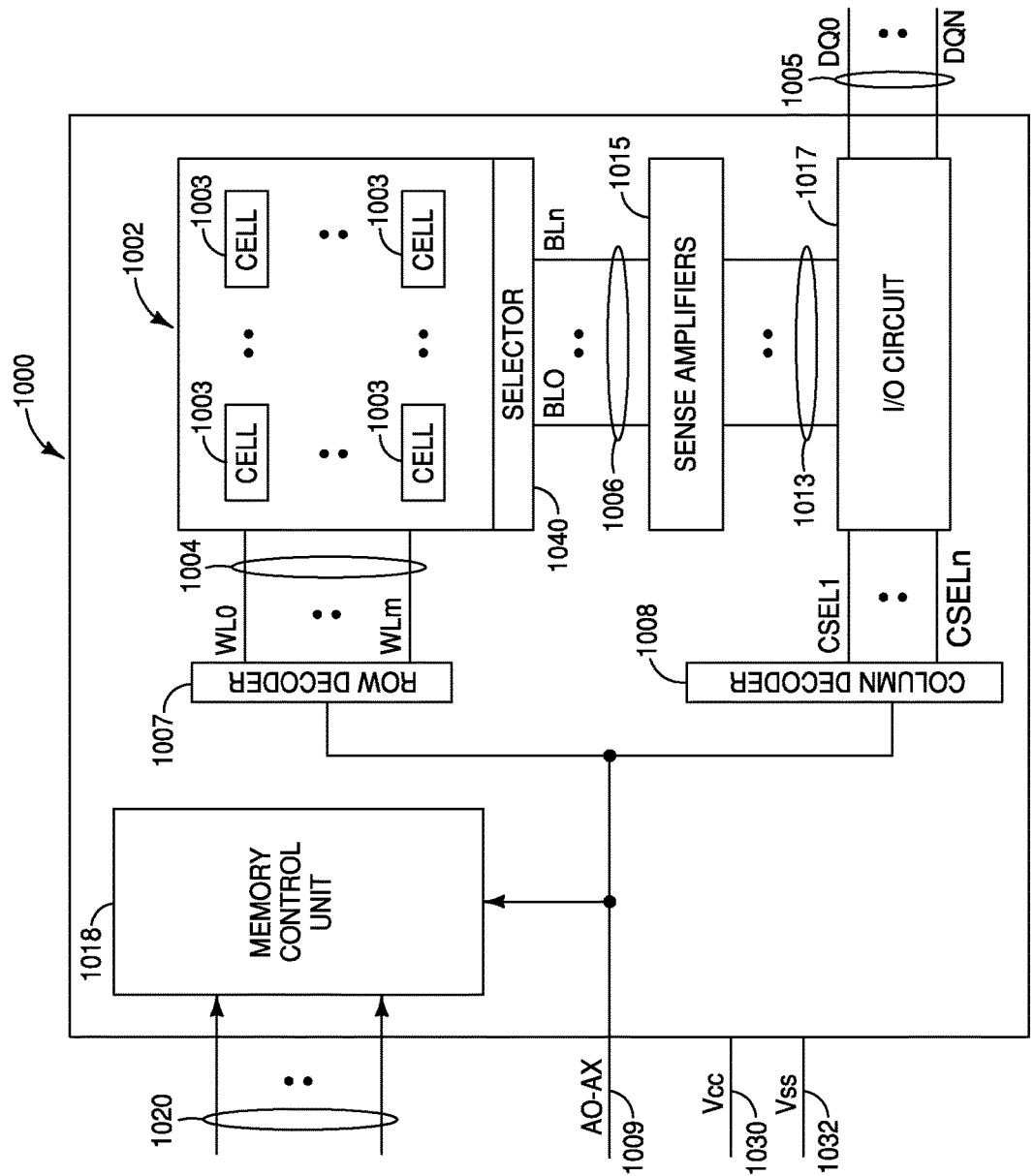
FIG. 1 shows a block diagram of a prior art memory device having a memory array with memory cells.
Figure 2:
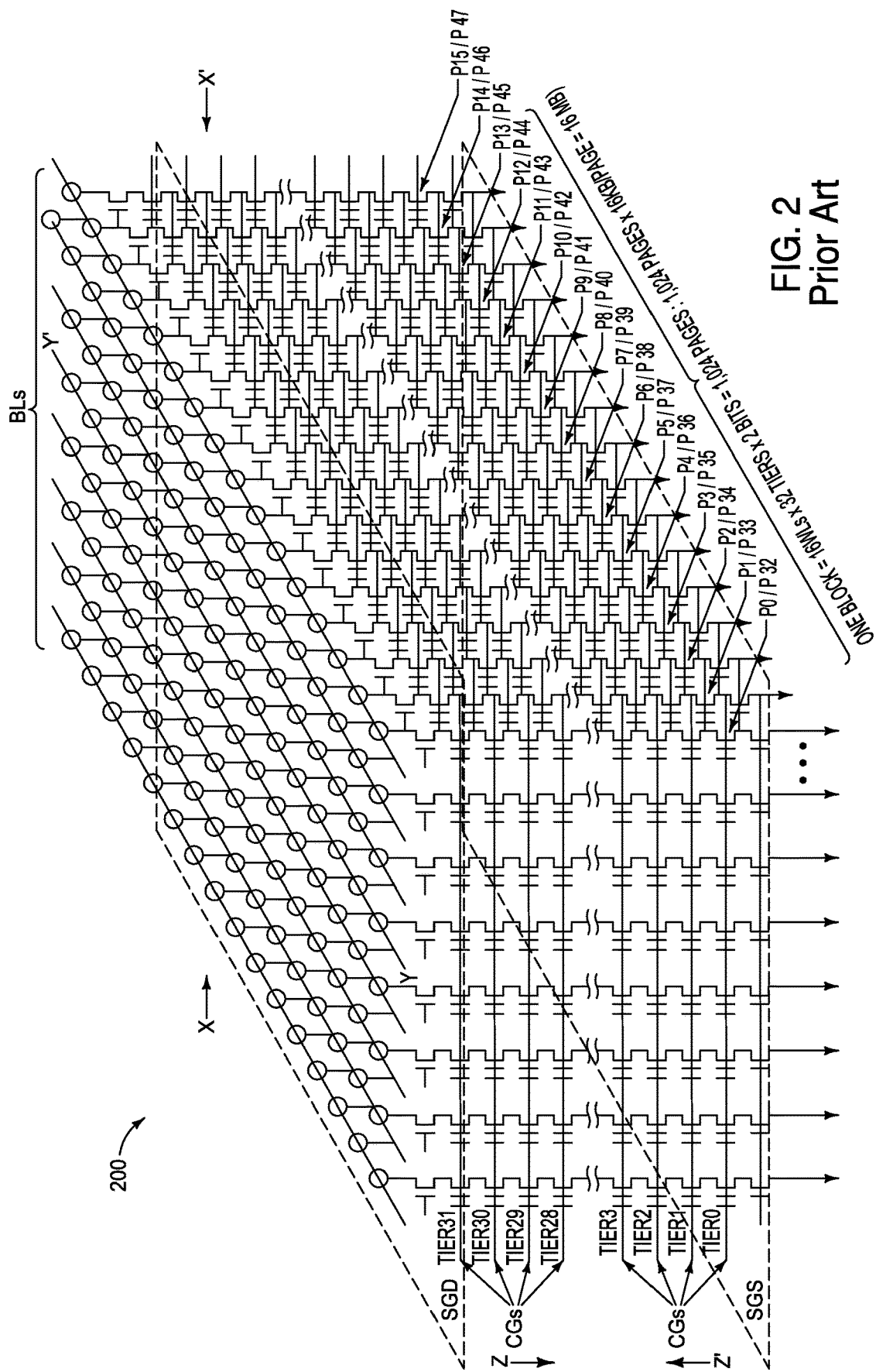
FIG. 2 shows a schematic diagram of the prior art memory array of FIG. 1 in the form of a 3D NAND memory device.
Figure 3:
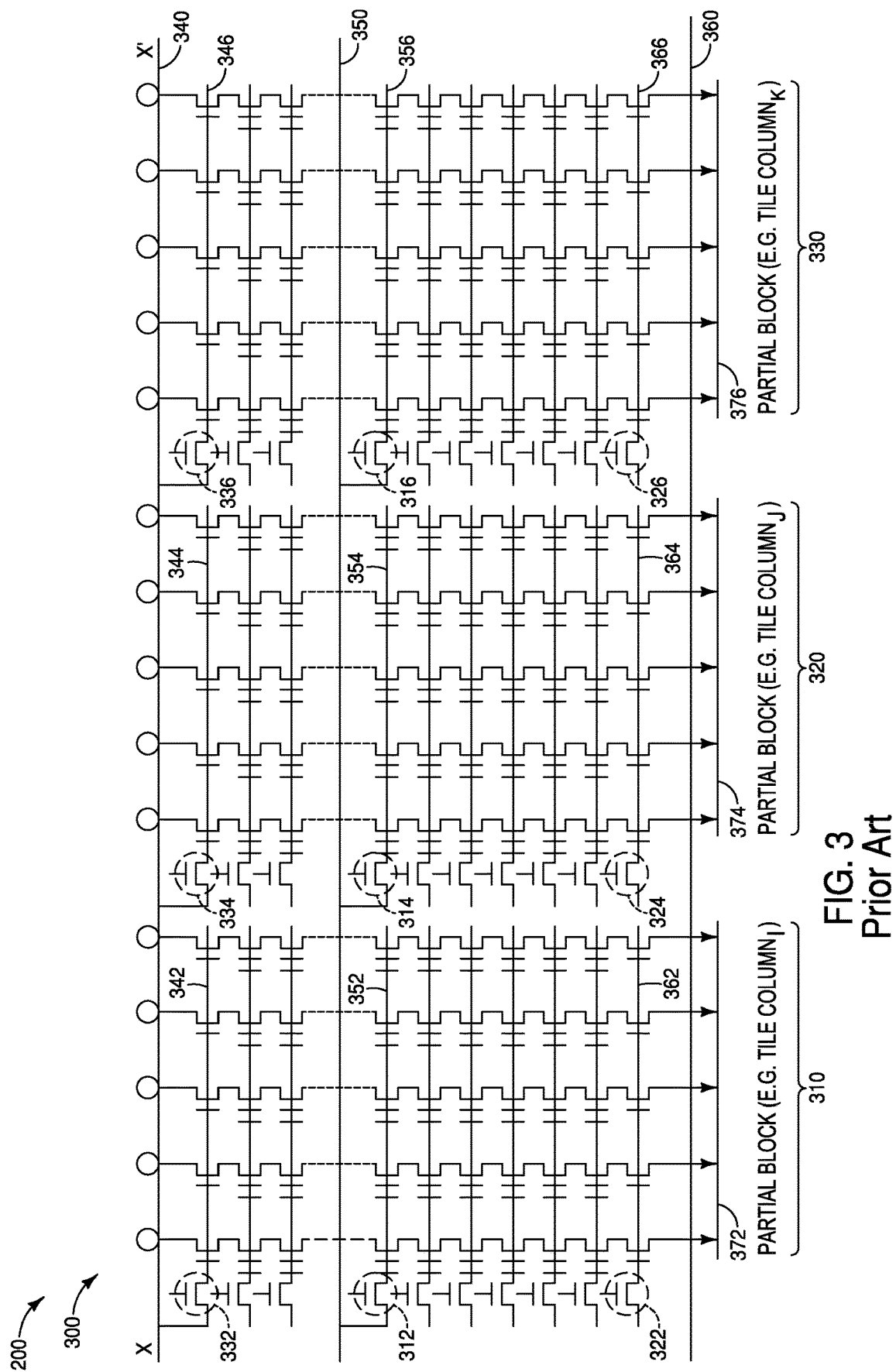
FIG. 3 shows a cross-sectional view of the prior art 3D NAND memory device of FIG. 2 in an X-X' direction.
Figure 4:
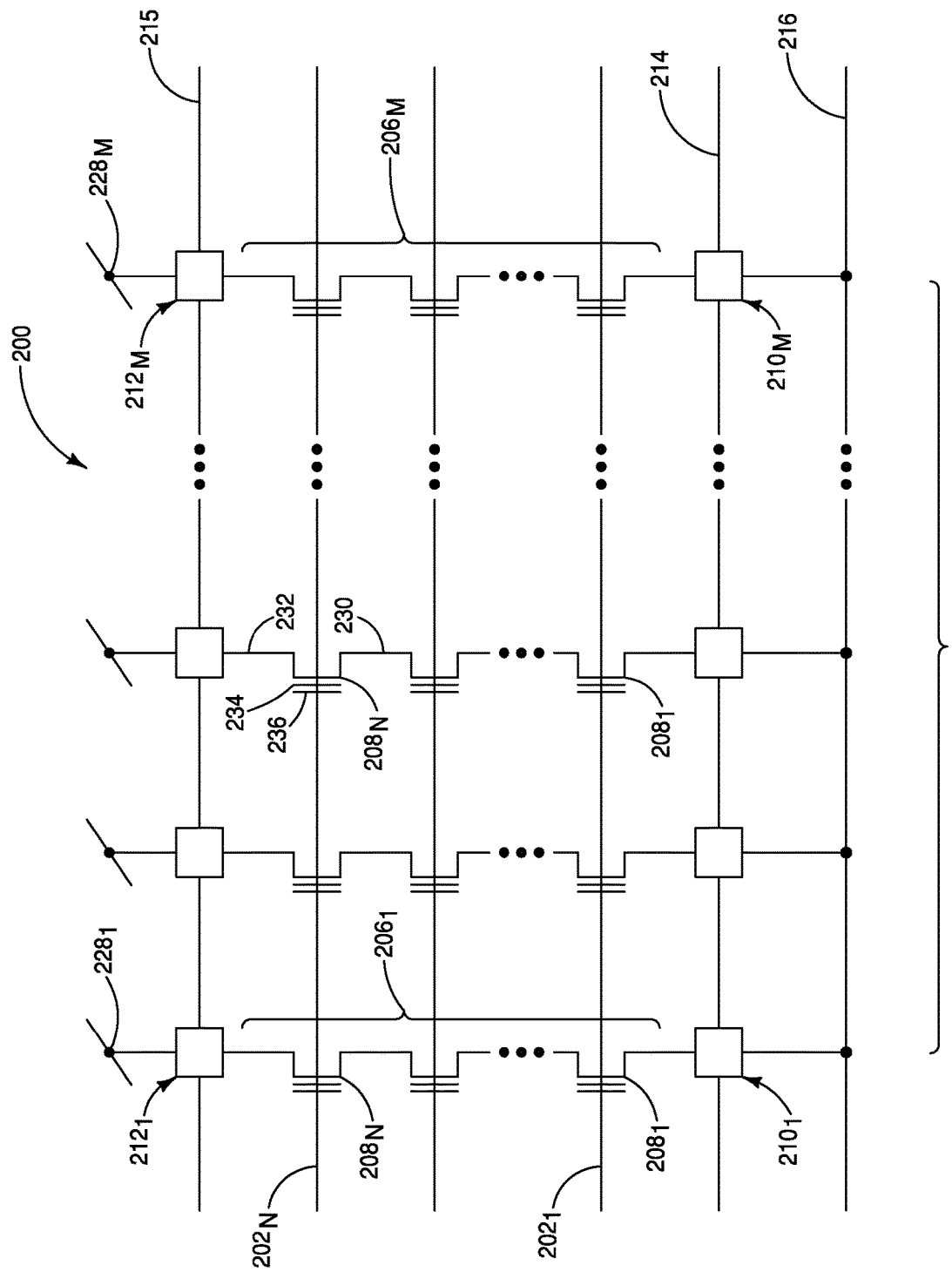
FIG. 4 is a schematic diagram of a prior art NAND memory array.

Some embodiments include integrated memory (e.g., three-dimensional NAND) having ruthenium incorporated into conductive wordline material and/or incorporated into conductive gates of memory devices. Example embodiments are described with reference to FIGS. 5-20.

Referring to FIG. 5, a construction (i.e., assembly, architecture, etc.) 10 includes a stack 12 of alternating first and second levels 14 and 16. The first levels 14 comprise a first material 18, and the second levels 16 comprise a second material 20. The first and second materials 18 and 20 may be any suitable materials. In some embodiments, the first material 18 may comprise, consist essentially of, or consist of silicon nitride; and the second material 20 may comprise, consist essentially of, or consist of silicon dioxide. The second material 20 may be electrically insulative, and in some embodiments may be referred to as an insulative material (or as an insulative second material). In such embodiments, the second levels 20 may be referred to as insulative levels.

The levels 14 and 16 may be of any suitable thicknesses; and may be the same thickness as one another, or may be different thicknesses relative to one another. In some embodiments, the levels 14 and 16 may have vertical thicknesses within a range of from about 3 nanometers (nm) to about 400 nm; within a range of from about 3 nm to about 50 nm, etc.

Some of the material 18 of the first levels 14 is ultimately replaced with conductive material of wordlines/memory cell gates. Accordingly, the levels 14 may be considered correspond to be memory cell levels (or wordline levels) of a NAND configuration. The NAND configuration will include strings of memory cells (i.e., NAND strings), with the number of memory cells in the strings being determined by the number of vertically-stacked levels 14. The NAND strings may comprise any suitable number of memory cell levels. For instance, the NAND strings may have 8 memory cell levels, 16 memory cell levels, 32 memory cell levels, 64 memory cell levels, 512 memory cell levels, 1024 memory cell levels, etc. Accordingly, the vertical stack 12 may extend outwardly beyond the illustrated region of the stack to include more vertically-stacked levels than those specifically illustrated in the diagram of FIG. 5.

The stack 12 is shown to be supported over a base 22. The base 22 may comprise semiconductor material; and may, for example, comprise, consist essentially of, or consist of monocrystalline silicon. The base 22 may be referred to as a semiconductor substrate. The term "semiconductor substrate" means any construction comprising semiconductive material, including, but not limited to, bulk semiconductive materials such as a semiconductive wafer (either alone or in assemblies comprising other materials), and semiconductive material layers (either alone or in assemblies comprising other materials). The term "substrate" refers to any supporting structure, including, but not limited to, the semiconductor substrates described above. In some applications, the base 22 may correspond to a semiconductor substrate containing one or more materials associated with integrated circuit fabrication. Such materials may include, for example, one or more of refractory metal materials, barrier materials, diffusion materials, insulator materials, etc.

A space is provided between the stack 12 and the base 22 to indicate that other components and materials may be provided between the stack 12 and the base 22. Such other components and materials may comprise additional levels of the stack, a source line level, source-side select gates (SGSs), etc.

Structures 28 are formed to extend through the stack 12.

The structures 28 include channel material structures (or channel structures) 29, which comprise channel material 30. In some embodiments, the stack 12 may be considered to be a vertically-extending stack, and the structures 29 may be considered to be vertically-extending channel material structures which pass through the stack 12. In some embodiments, the structures 29 may be referred to as channel-material-pillars.

The channel material 30 is semiconductor material; and may comprise any suitable composition or combination of compositions. For instance, the channel material 30 may comprise one or more of silicon, germanium, III/V semiconductor materials (e.g., gallium phosphide), semiconductor oxides, etc.; with the term III/V semiconductor material referring to semiconductor materials comprising elements selected from groups III and V of the periodic table (with groups III and V being old nomenclature, and now being referred to as groups 13 and 15).

Tunneling material (sometimes referred to as gate dielectric material) 32, charge-storage material 34 and charge-blocking material 36 are between the channel material 30 and the vertically-stacked levels 16/18. The tunneling material, charge-storage material and charge-blocking material may comprise any suitable compositions or combinations of compositions.

In some embodiments, the tunneling material 32 may comprise, for example, one or more of silicon dioxide, aluminum oxide, hafnium oxide, zirconium oxide, etc.

In some embodiments, the charge-storage material 34 may comprise charge-trapping materials, such as silicon nitride, silicon oxynitride, conductive nanodots, etc. In alternative embodiments, the charge-storage material 34 may be configured to include floating gate material (such as, for example, polycrystalline silicon).

In some embodiments, the charge-blocking material 36 may comprise one or more of silicon dioxide, aluminum oxide, hafnium oxide, zirconium oxide, etc.

In some embodiments, the tunneling material 32 may be considered to comprise tunneling regions 15 alongside the wordline levels 14, the charge-storage material 34 may be considered to comprise charge-storage regions 17 alongside the wordline levels 14, and the charge-blocking material 36 may be considered to comprise charge-blocking regions 19 alongside the wordline levels 14.

In the illustrated embodiment, the channel material 30 is configured as annular rings (visible relative to FIG. 5A) within each of the structures 28. Insulative material 38 fills such annular rings. The insulative material 38 may comprise any suitable composition(s); and may, for example, comprise, consist essentially of, or consist of silicon dioxide. The illustrated channel structures 29 may be considered to comprise hollow channel configurations, in that the insulative material 38 is provided within "hollows" in the annular ring-shaped channel configurations. In other embodiments (not shown), the channel material may be configured as a solid pillar configuration.

Figure 5A:
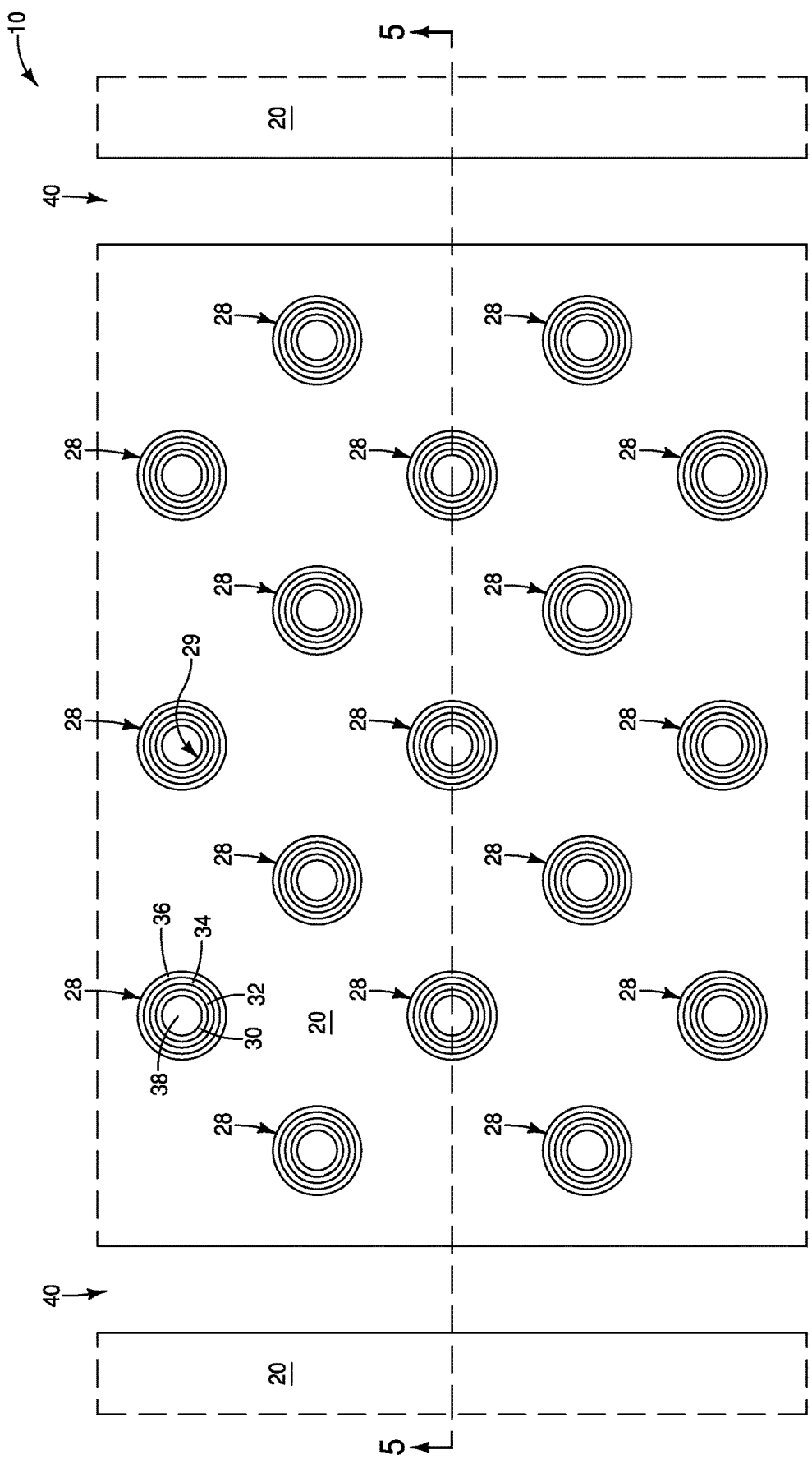
FIG. 5A is a diagrammatic top-down view along the line 5A-5A of FIG. 5.

The structures 28 may be considered to comprise all of the materials 30, 32, 34, 36 and 38 in combination. The top view of FIG. 5A shows that the structures 28 may be arranged in a hexagonally-packed pattern.

In some embodiments, formation of the structures 28 may be considered to include forming the tunneling material 32 adjacent the channel material 30 of the channel-material-pillars 29, forming the charge-storage material 34 adjacent the tunneling material 32, and forming the charge-blocking material 36 adjacent the charge-storage material 34.

Slits (trenches) 40 are formed to extend through the stack 12.

Figure 6:
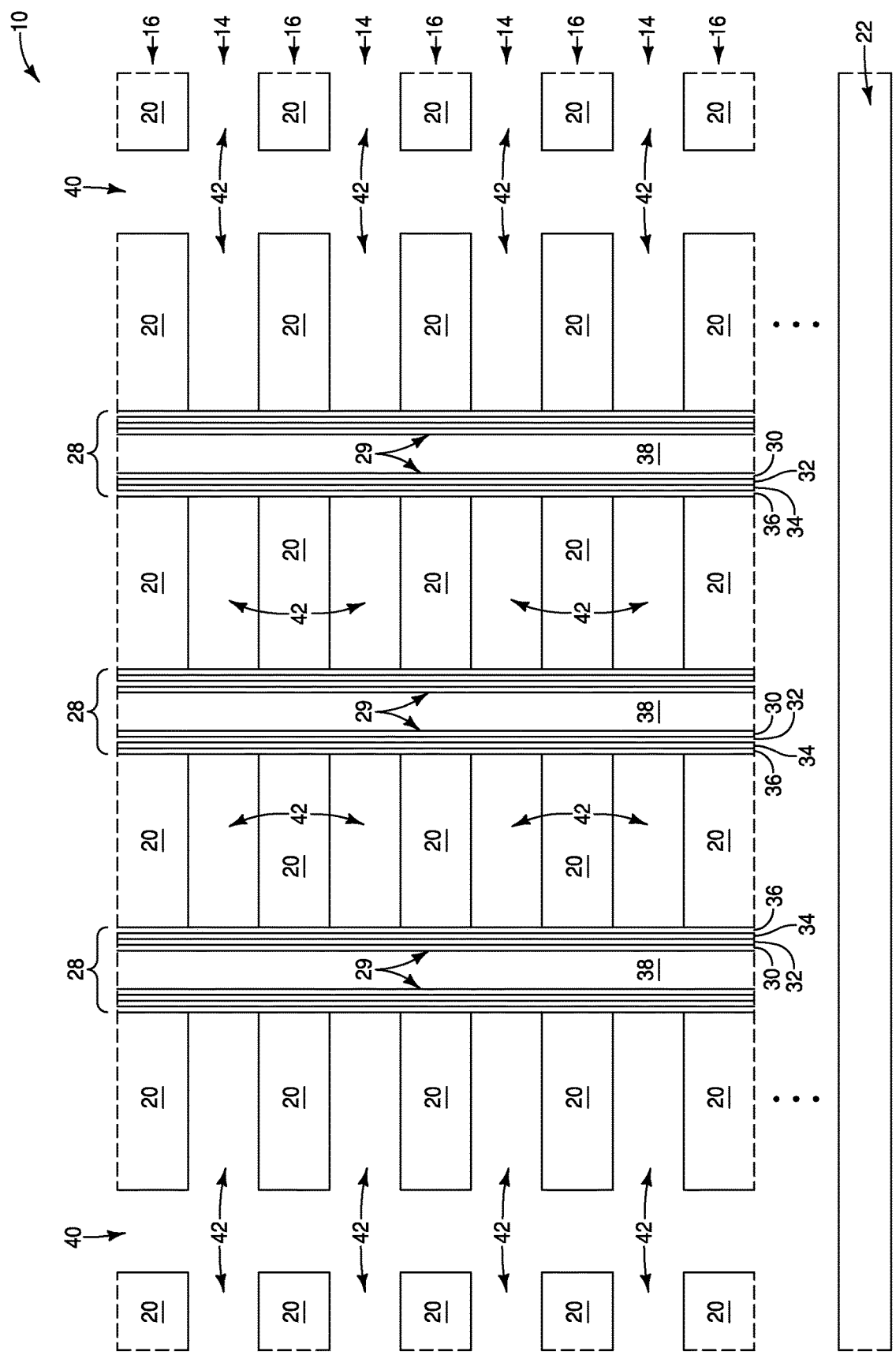

Referring to FIG. 6, the first material 18 (FIG. 5) of the first levels 14 is removed to form voids (cavities) 42 along the first levels 14.

Figure 7:
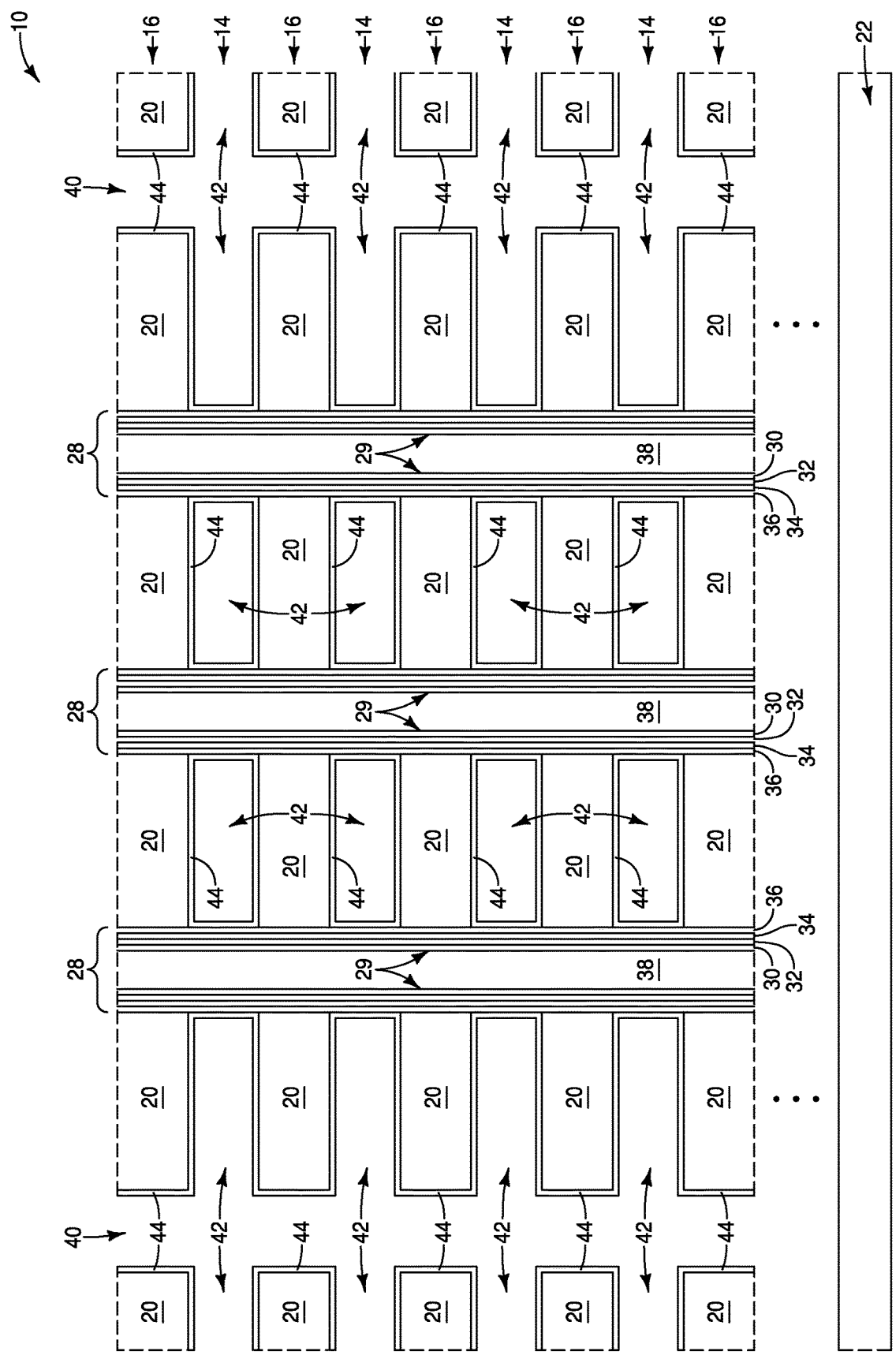

Referring to FIG. 7, dielectric barrier material 44 is formed within the voids 42 to line the voids.

The dielectric barrier material 44 may comprise any suitable composition(s); and in some embodiments may comprise one or more high-k materials (with the term high-k meaning a dielectric constant greater than that of silicon dioxide). Example compositions which may be incorporated into the dielectric barrier material are hafnium oxide, zirconium oxide, aluminum oxide, hafnium silicate, zirconium silicate, titanium oxide, gadolinium oxide, niobium oxide, tantalum oxide, etc.

Figure 8:
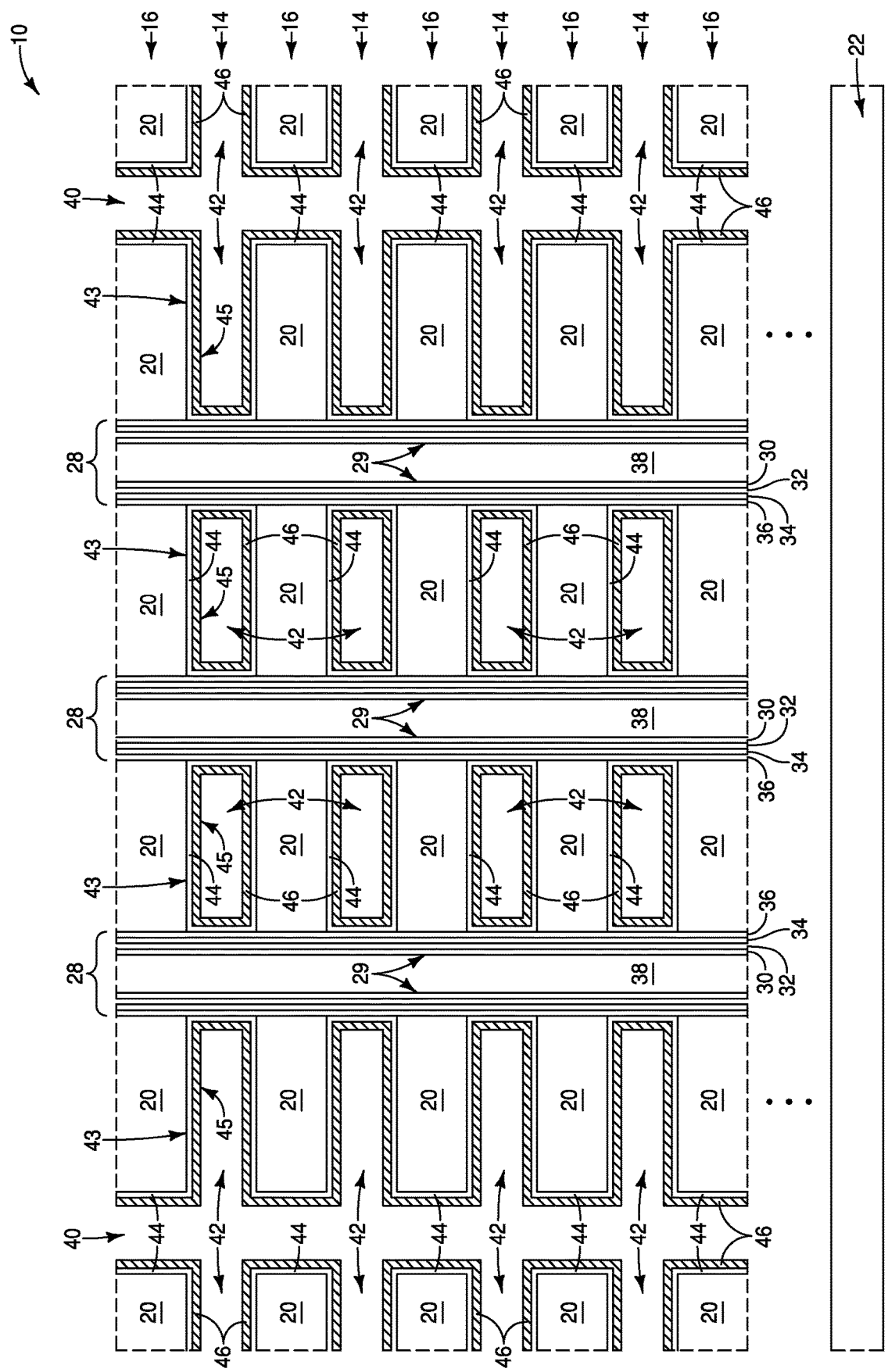

Referring to FIG. 8, first conductive material 46 is formed within the voids 42 and over the dielectric barrier material 44 (i.e., is formed within the voids 42 after such voids are lined with the dielectric barrier material 44). The first conductive material 46 may comprise, consist essentially of, or consist of ruthenium.

The ruthenium-containing material 46 may advantageously adhere well to the high-k dielectric material of the dielectric barrier material 44.

In the shown embodiment, the ruthenium-containing material 46 only partially fills the voids 46, and accordingly lines the voids. In some embodiments, the dielectric barrier material 44 may be considered to form first liners 43, and the ruthenium-containing material 46 may be considered to form second liners 45 which are over and directly against the first liners.

Figure 9:
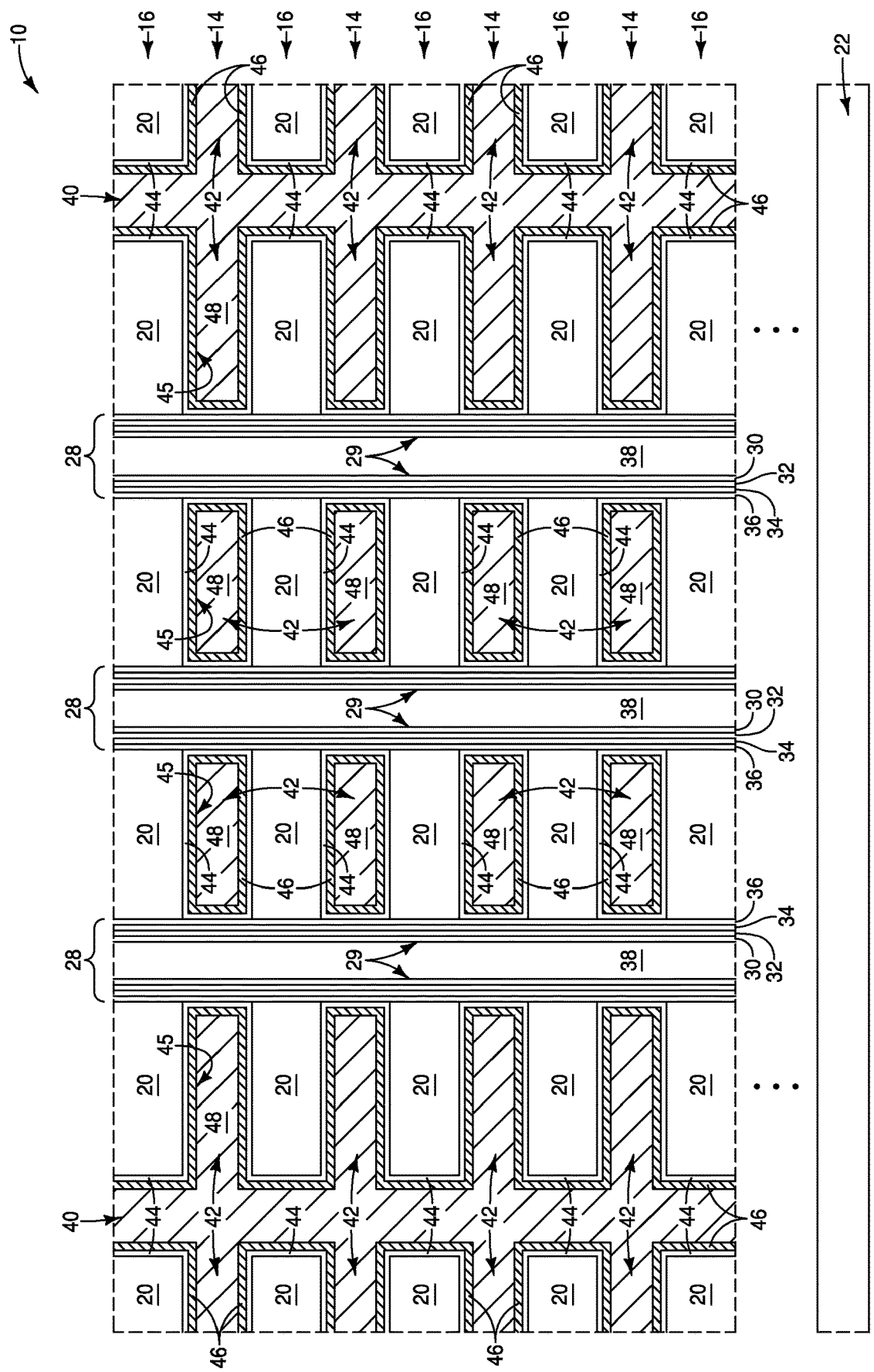

Referring to FIG. 9, conductive core material 48 is formed within the voids 42, and fills the voids. The conductive core material 48 is formed over and directly against the ruthenium-containing material 46; and in some embodiments may be considered to be formed directly against the second liners (i.e., the ruthenium-containing liners) 45.

The conductive core material 48 may comprise any suitable electrically conductive composition(s), such as, for example, one or more of various metals (e.g., titanium, tungsten, cobalt, nickel, platinum, ruthenium, etc.), metal-containing compositions (e.g., metal silicide, metal nitride, metal carbide, etc.), and/or conductively-doped semiconductor materials (e.g., conductively-doped silicon, conductively-doped germanium, etc.). In some embodiments, the conductive core material 48 does not comprise ruthenium. In some embodiments, the conductive core material 48 may comprise, consist essentially of, or consist of one or more metals; and may, for example, comprise, consist essentially of, or consist of one or both of tungsten and molybdenum.

Figure 10:
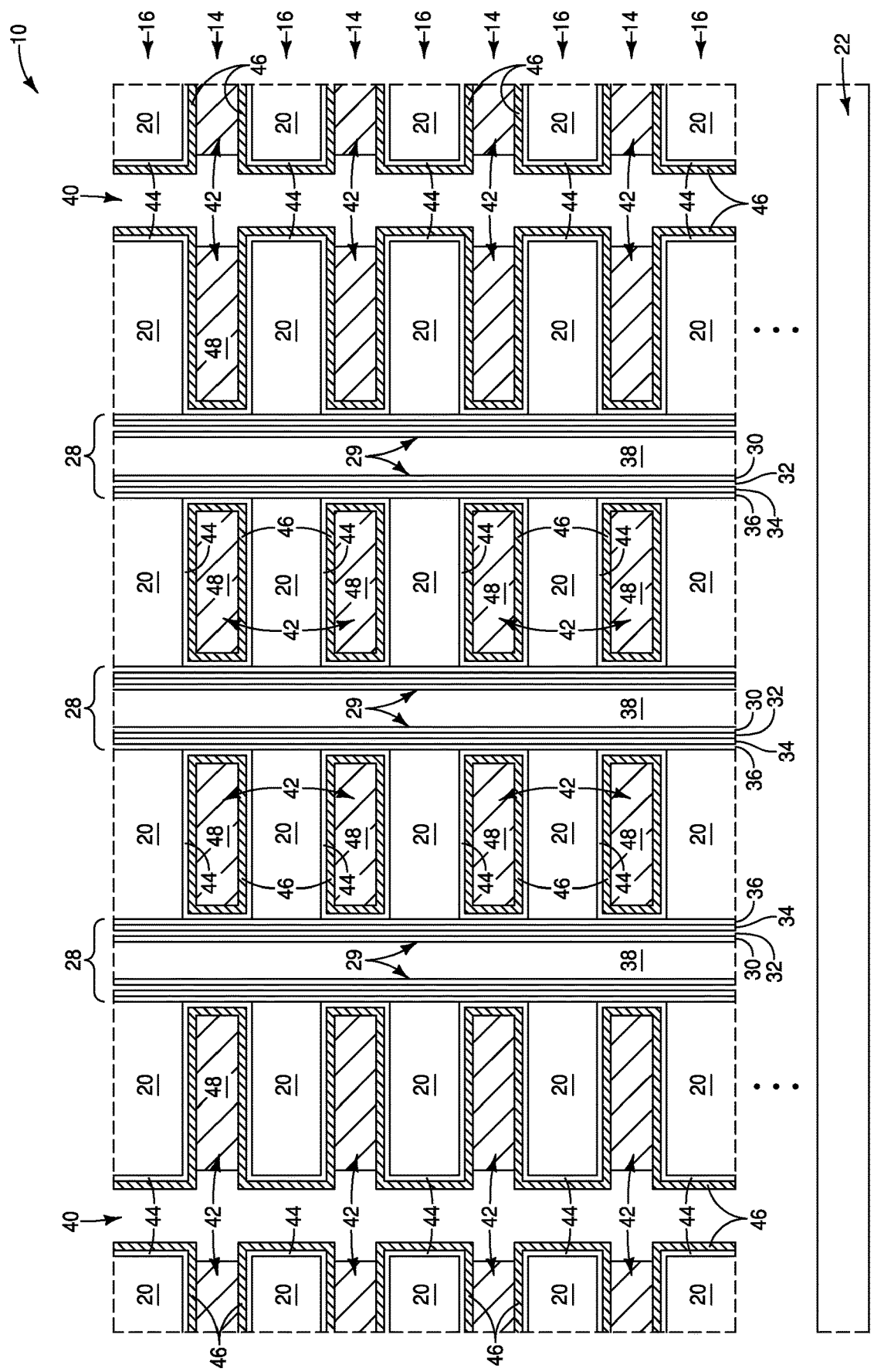

Referring to FIG. 10, the conductive core material 48 is recessed within the voids 42 in locations along the slits 40 with a first etch (e.g., a wet etch utilizing ammonium hydroxide). In some embodiments, the conductive core material 48 may be removed selectively relative to the ruthenium-containing material 46. For purposes of interpreting this disclosure and the claims that follow, a first material is considered to be removed selectively relative to a second material if the first material is removed under conditions which etch the first material faster than the second material. This can include, but is not limited to, applications having etches which are 100% selective for the first material relative to the second material.

Figure 11:
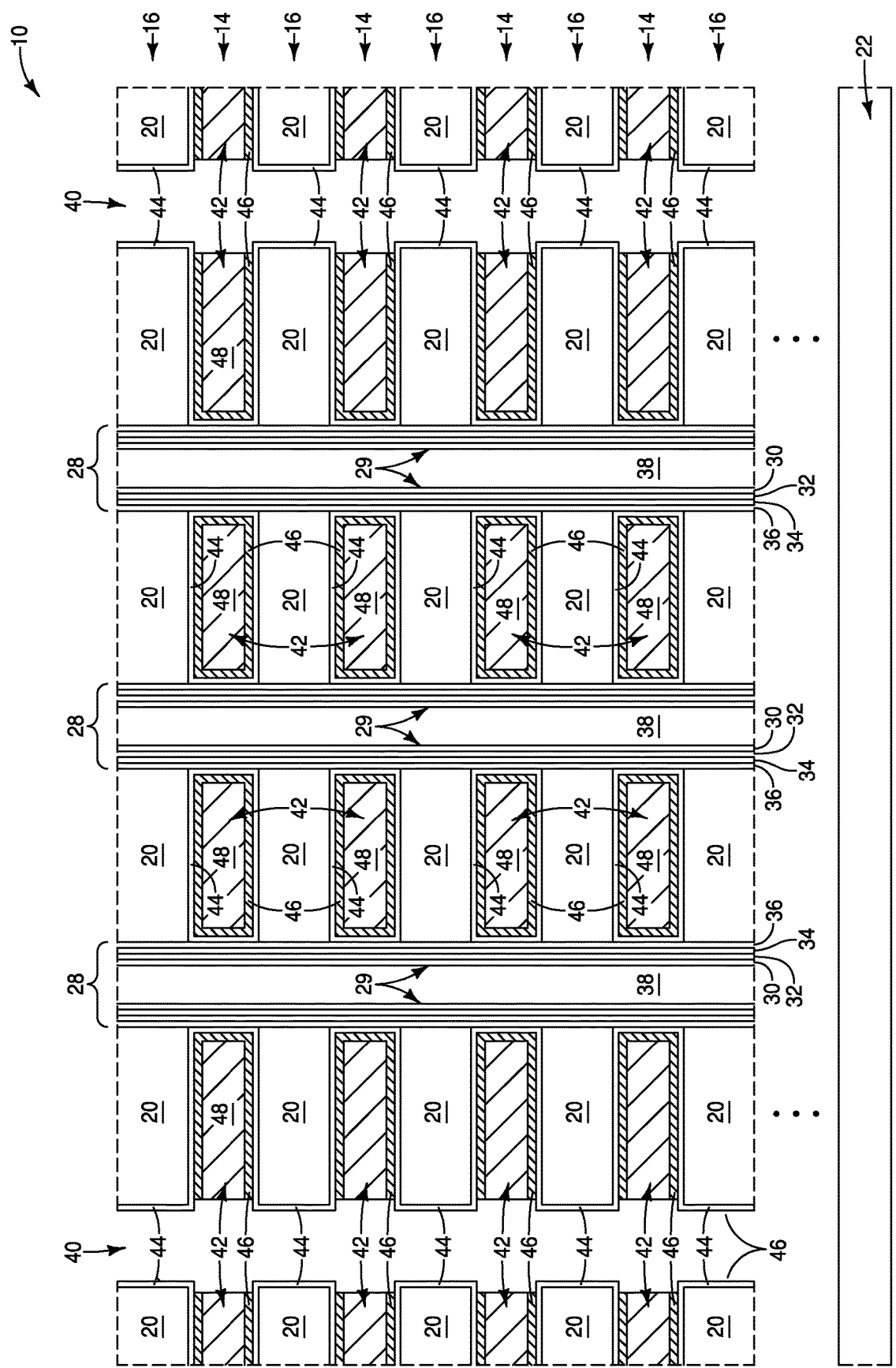

Referring to FIG. 11, the ruthenium-containing material 46 is recessed within the voids 42 in locations along the slits 40 with a second etch which is different from the first etch of FIG. 10. In some embodiments, the second etch may utilize an oxidative plasma; such as, for example, a plasma utilizing one or both of $O_2$ and $O_3$.

Figure 12:
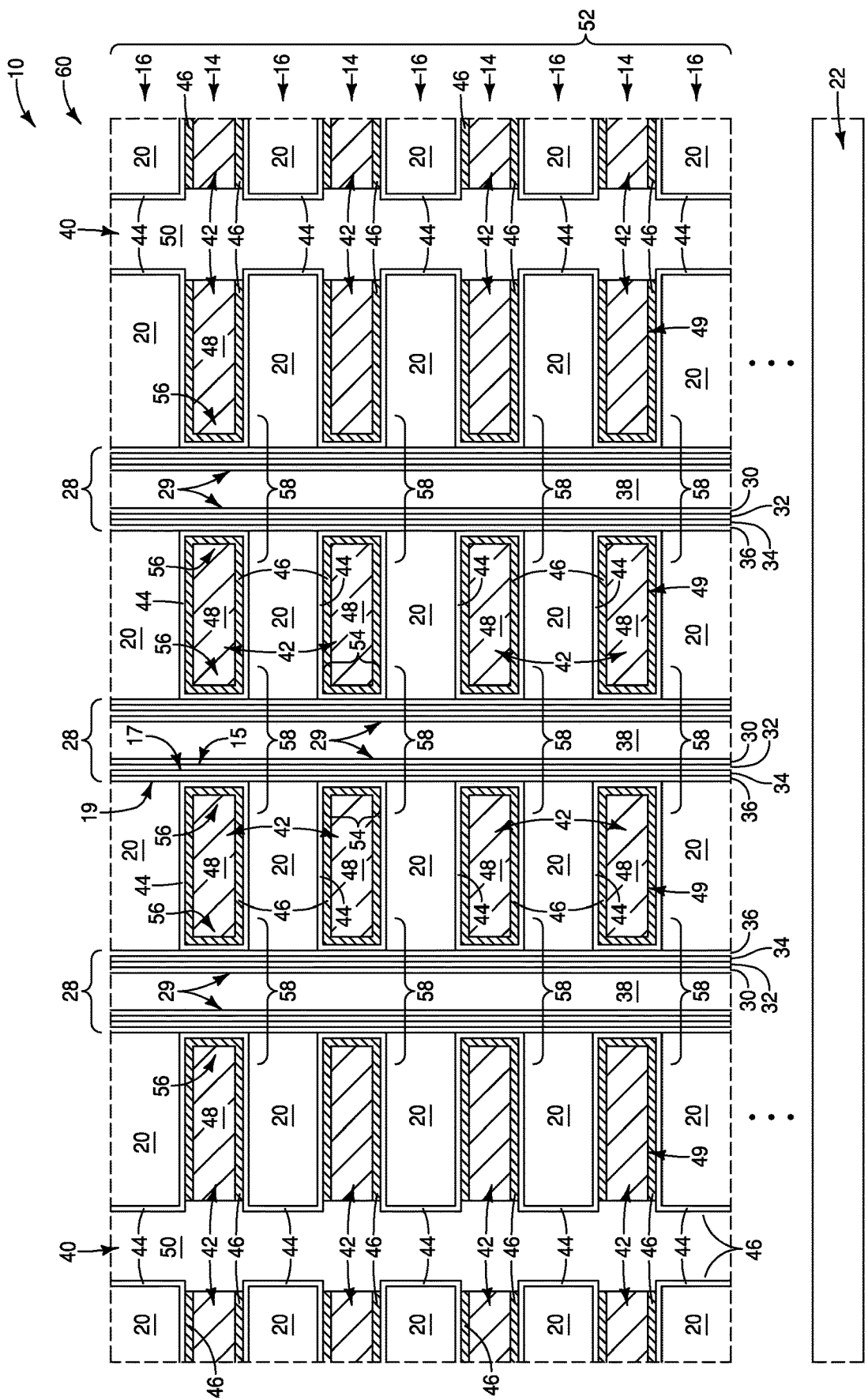

Referring to FIG. 12, insulative material 50 is formed within the slits 40. The insulative material 50 may comprise any suitable composition(s), and in some embodiments may comprise, consist essentially of, or consist of silicon dioxide.

The levels 14 are conductive levels at the processing stage of FIG. 12; and may be referred to as wordline levels, memory cell levels, etc.

The insulative levels 16 and wordline levels 14 alternate with one another at the processing stage of FIG. 12, and together form a vertical stack 52. The structures 28 extend through the vertical stack 52. Accordingly, the channel structures 29 extend through the stack 52.

The conductive materials 48 and 46 may be together considered to form conductive wordline material 54 (which may be also referred to as conductive gate material).

The wordline levels 14 comprise conductive gates 56 (only some of which are labeled) adjacent the channel material structures 29. The conductive gates 56 may be considered to comprise the conductive gate material 54, with such conductive gate material including ruthenium from the ruthenium-containing material 46. The conductive gates 56, together with regions of the dielectric-barrier material 44, charge-blocking material 36, charge-storage material 34, tunneling material 32 and channel material 30 form memory cells 58. Such memory cells are incorporated into a three-dimensional NAND memory array 60 analogous to the NAND memory arrays described above with reference to FIGS. 1-4. The memory cells 58 are all substantially identical to one another (with the term "substantially identical" meaning identical to within reasonable tolerances of fabrication and measurement).

In operation, the charge-storage material 34 may be configured to store information in the memory cells 58. The value (with the term "value" representing one bit or multiple bits) of information stored in an individual memory cell may be based on the amount of charge (e.g., the number of electrons) stored in a charge-storage region of the memory cell. The amount of charge within an individual charge-storage region may be controlled (e.g., increased or decreased), at least in part, based on the value of voltage applied to an associated gate 56, and/or based on the value of voltage applied to an associated channel material 30.

The tunneling material 32 forms tunneling regions of the memory cells 58. Such tunneling regions may be configured to allow desired migration (e.g., transportation) of charge (e.g., electrons) between the charge-storage material 34 and the channel material 30. The tunneling regions may be configured (i.e., engineered) to achieve a selected criterion, such as, for example, but not limited to, an equivalent oxide thickness (EOT). The EOT quantifies the electrical properties of the tunneling regions (e.g., capacitance) in terms of a representative physical thickness. For example, EOT may be defined as the thickness of a theoretical silicon dioxide layer that would be required to have the same capacitance density as a given dielectric, ignoring leakage current and reliability considerations.

The charge-blocking material 36 is adjacent to the charge-storage material 34, and may provide a mechanism to block charge from flowing from the charge-storage material 34 to the associated gates 56.

The dielectric-barrier material 44 is provided between the charge-blocking material 36 and the associated gates 56, and may be utilized to inhibit back-tunneling of charge carriers from the gates 56 toward the charge-storage material 34. In some embodiments, the dielectric-barrier material 44 may be considered to form dielectric-barrier regions within the memory cells 58.

In some embodiments, the memory cells 58 may be considered to comprise tunneling regions 15, charge-storage regions 17, and charge-blocking regions 19. The charge-storage regions 17 are between the conductive wordline material 54 and the channel structures 29, and the charge-blocking regions 19 are between the charge-storage regions 17 and the conductive wordline material 54.

An advantage of including the ruthenium-containing material 46 within the conductive wordline material 54 is that such may reduce back tunneling from the gates 56 to the charge-storage regions 17 as compared to conventional configurations lacking the ruthenium-containing material.

Another advantage of including the ruthenium-containing material may be that such provides lower sheet resistance as compared to conventional materials, which may enable the conductive wordlines of levels 14 to be formed thinner than conventional wordlines; improving scalability as compared to conventional architectures.

In some embodiments, the conductive core material 48 of FIG. 12 may be considered to have an outer periphery 49. The ruthenium-containing material 46 may be considered to be a second conductive material adjacent the outer periphery 49 of the conductive core material 48.

Another example embodiment method for fabricating example memory cells is described with reference to FIGS. 13-15.

Figure 13:
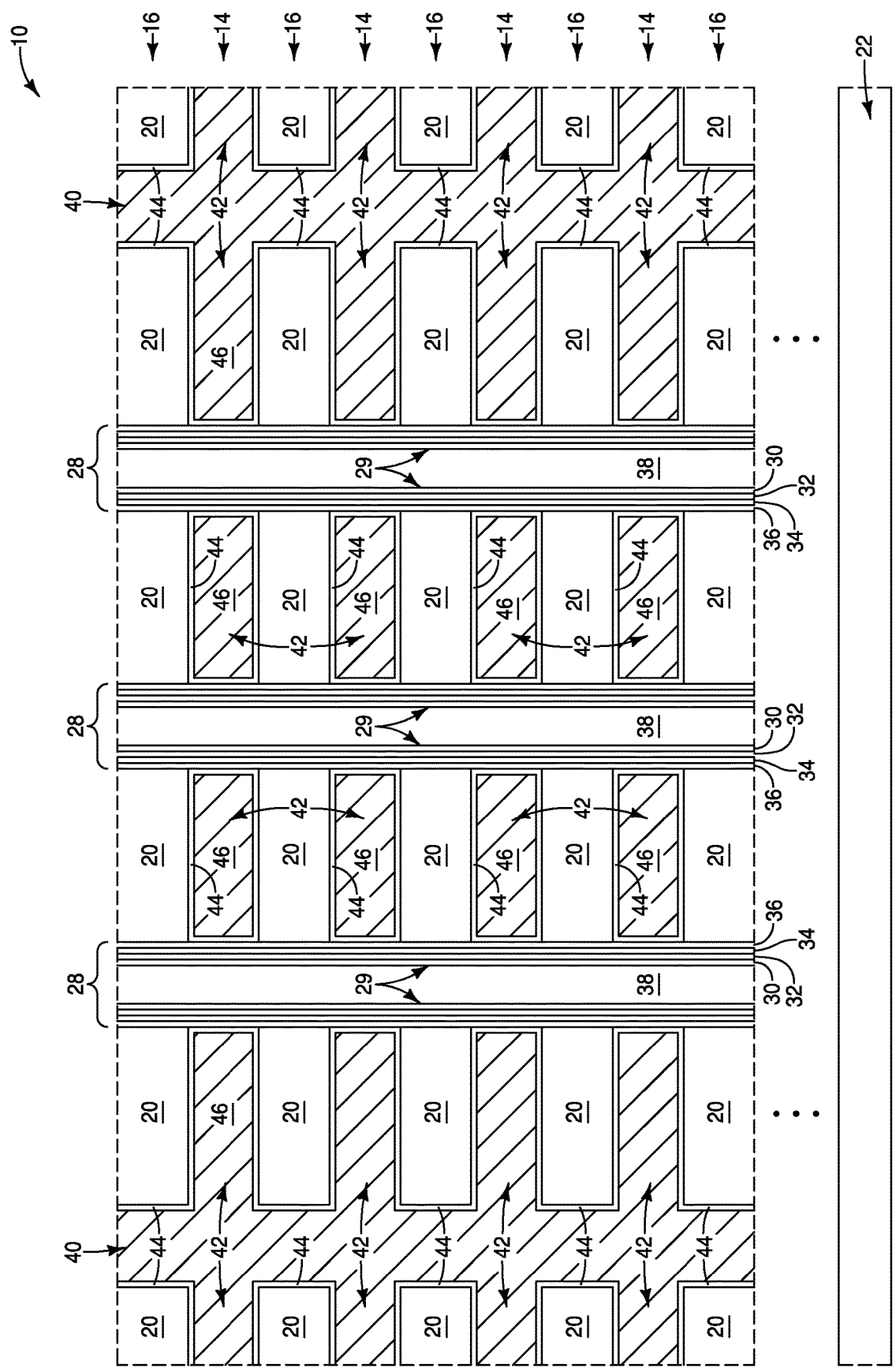
FIGS. 13-15 are diagrammatic cross-sectional side views of a region of an integrated assembly at example process stages of an example method for forming an example memory array. The process stage of FIG. 13 may follow that of FIG. 7.

Referring to FIG. 13, the assembly 10 is shown at a process stage which may follow that of FIG. 7. The ruthenium-containing material 46 entirely fills the voids 42.

Figure 14:
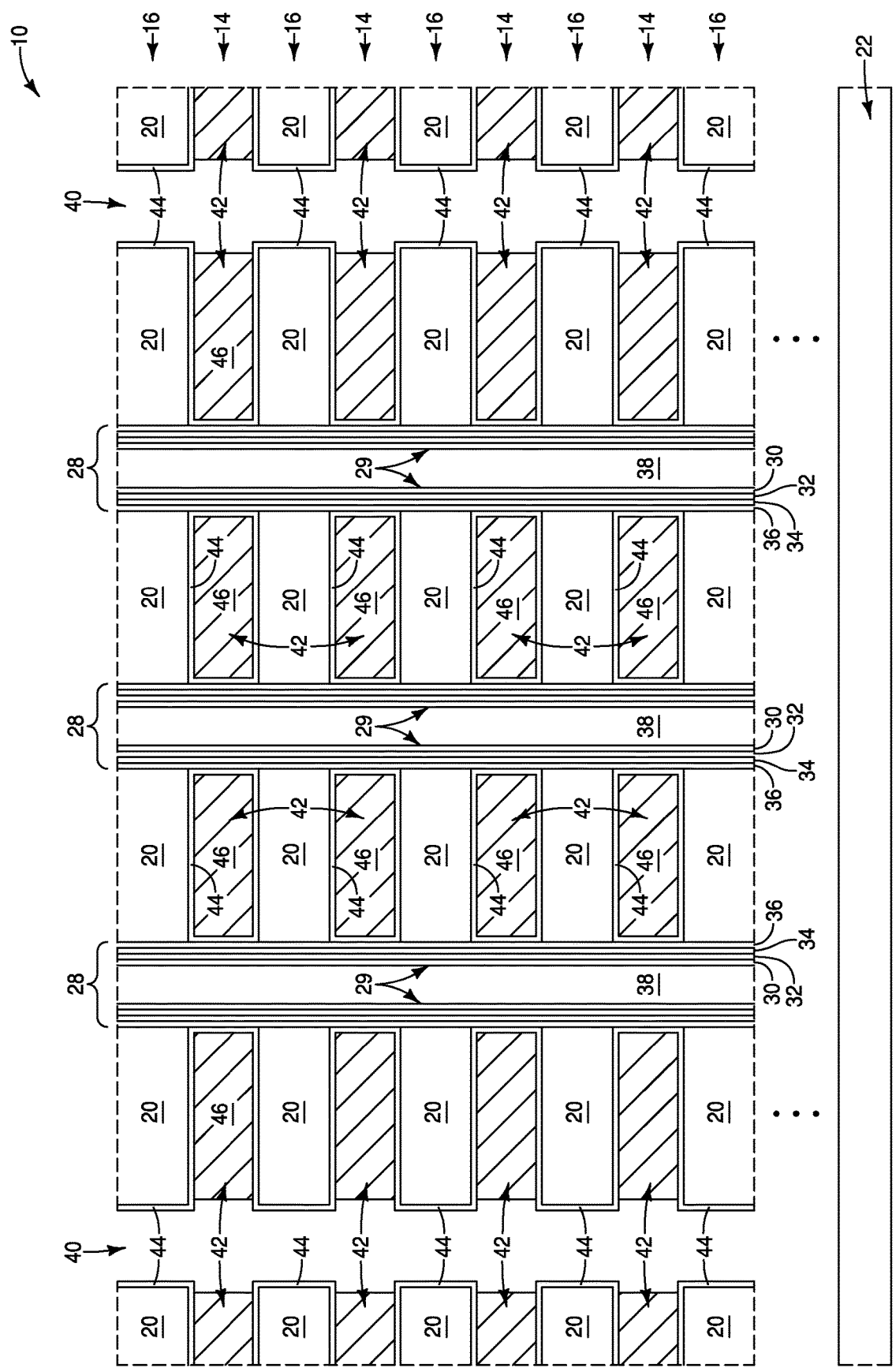

Referring to FIG. 14, the ruthenium-containing material 46 is removed from within the slits 40, and is recessed within the voids 42 in locations adjacent the slits 40. The recessing of the ruthenium-containing material may utilize an oxidative plasma of the type described above with reference to FIG. 11.

Figure 15:
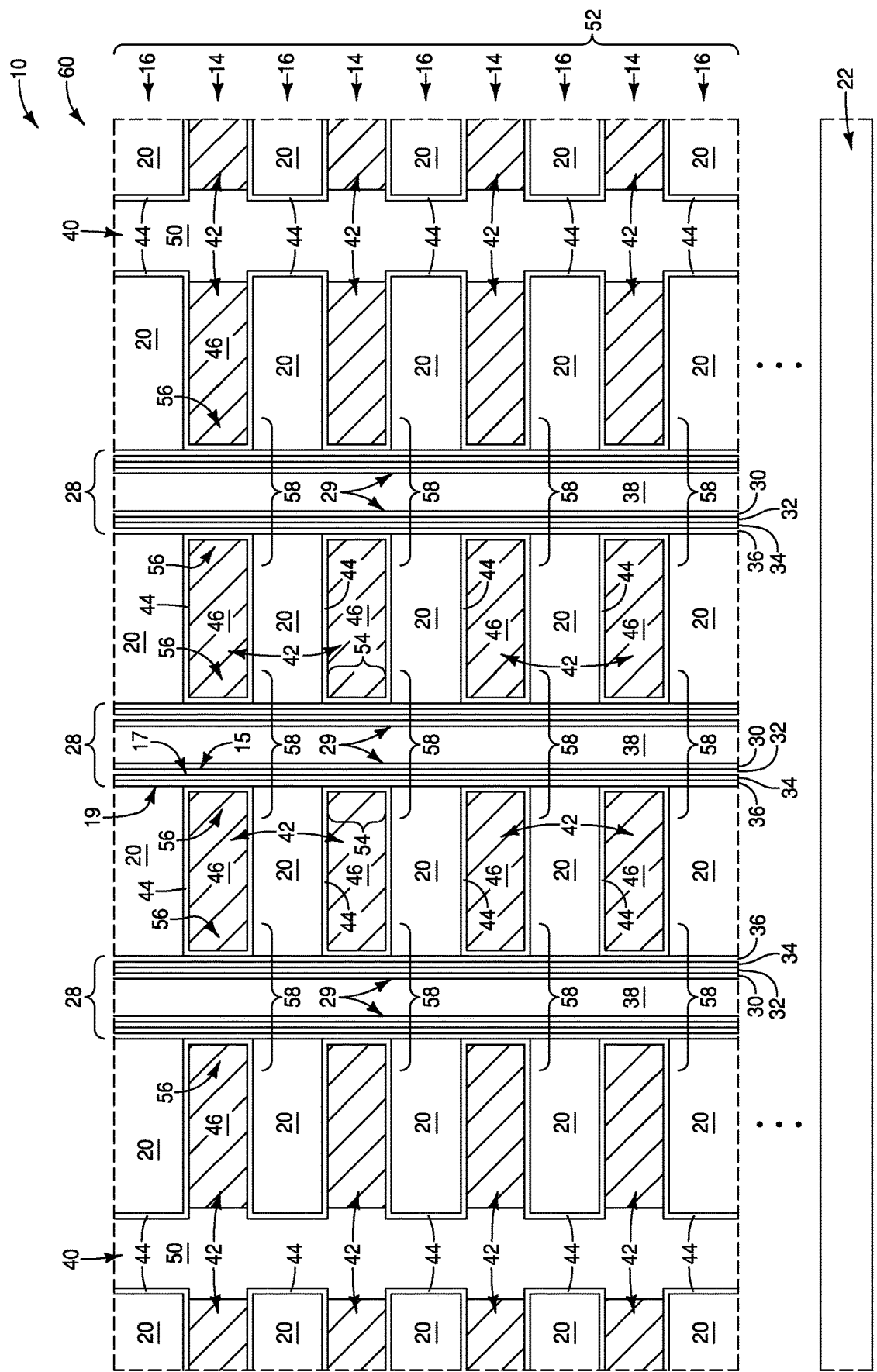

Referring to FIG. 15, the insulative material 50 is formed within the slits 40.

The assembly 10 of FIG. 15 includes the stack 52 of alternating conductive wordline levels 14 and insulative levels 16. The conductive wordline levels 14 comprise conductive wordline material (conductive gate material) 54 which comprises only the ruthenium-containing material 46. In some embodiments, the conductive wordline material (conductive gate material) 54 may comprise, consist essentially of, or consist of ruthenium.

The conductive wordline levels 14 are incorporated into a NAND memory array 60 analogous to that described above with reference to FIG. 12. The memory array includes a plurality of memory cells 58. Regions of the conductive material 54 form gates 56 of the memory cells.

The utilization of wordline material 54 comprising only ruthenium (i.e., consisting of ruthenium) may enable sheet resistance of the wordline levels to be substantially reduced relative to conventional NAND configurations, which may enable higher integration to be achieved utilizing the NAND memory configurations described herein as compared to conventional NAND memory configurations.

Another example embodiment method for fabricating example memory cells is described with reference to FIGS. 16-20.

Figure 16:
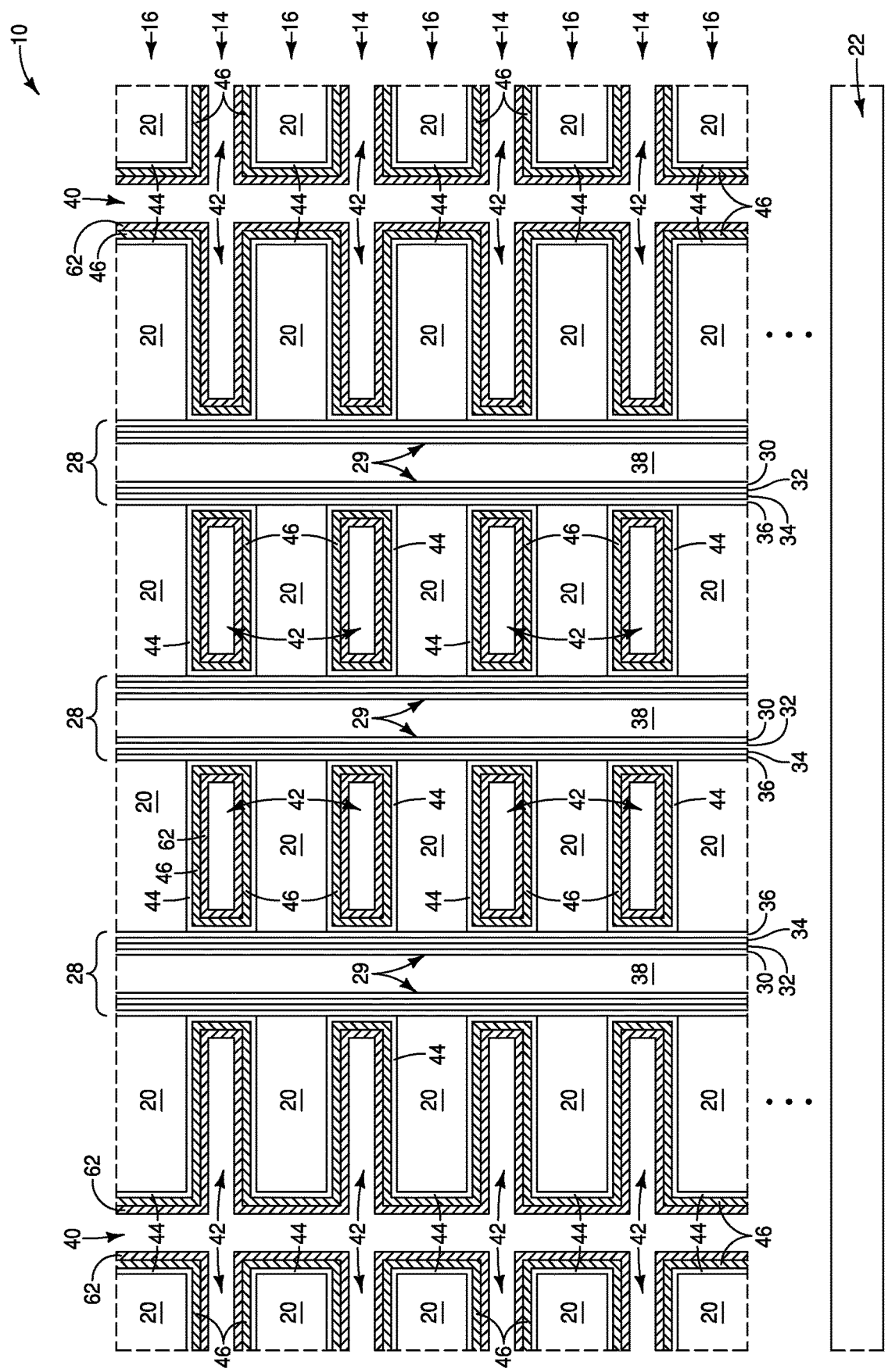
FIGS. 16-20 are diagrammatic cross-sectional side views of a region of an integrated assembly at example process stages of an example method for forming an example memory array. The process stage of FIG. 16 may follow that of FIG. 7.

Referring to FIG. 16, the assembly 10 is shown at a process stage which may follow that of FIG. 7. The ruthenium-containing material 46 lines the voids 42, and another conductive material 62 is formed to further line the voids. The conductive material 62 may comprise any suitable composition(s); and in some embodiments may comprise, consist essentially of, or consist of one or more metal nitrides (e.g., titanium nitride, tungsten nitride, etc.).

Figure 17:
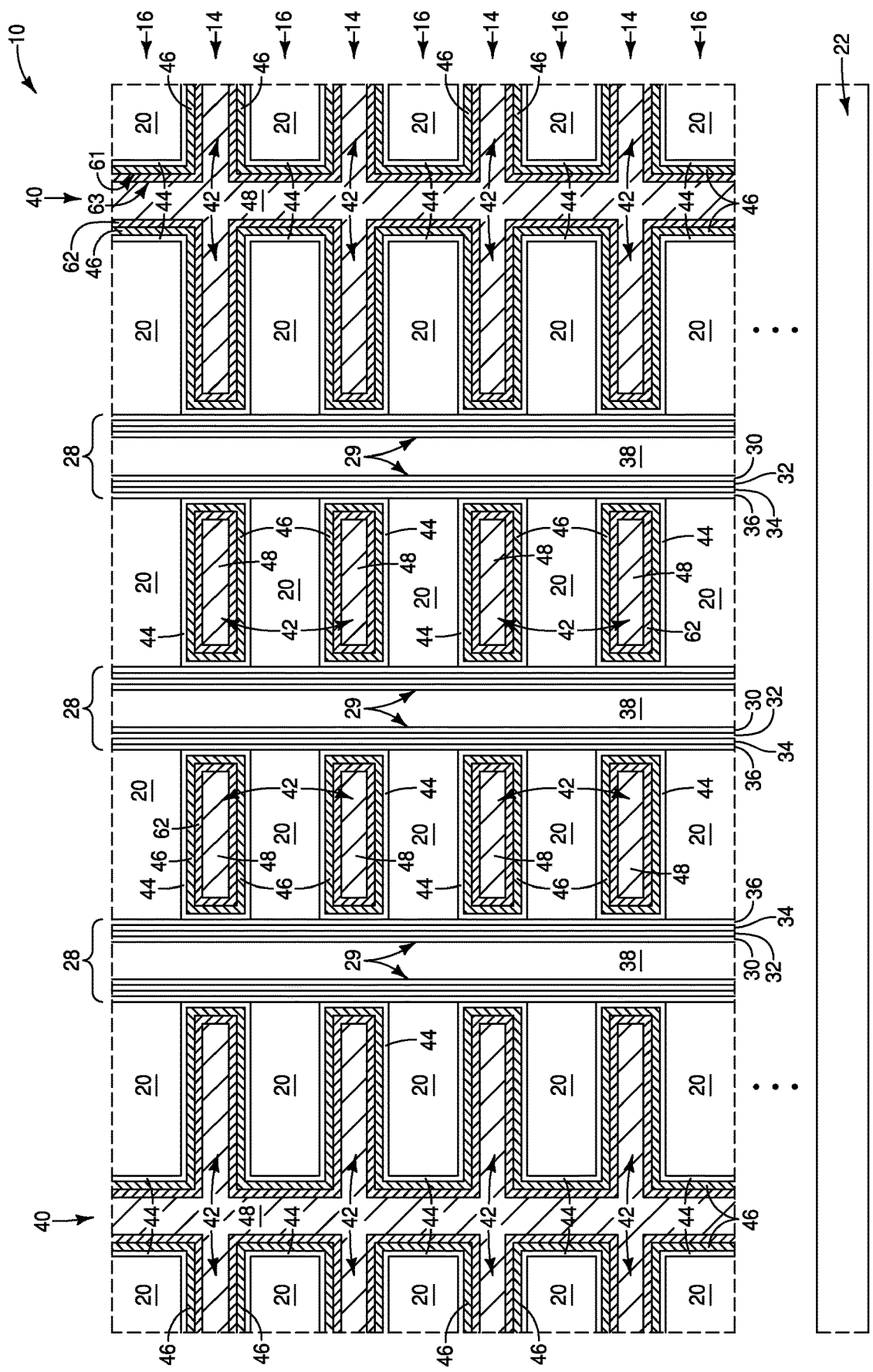

Referring to FIG. 17, the conductive core material 48 is formed over the conductive material 62, and fills the voids 42. In some embodiments, the conductive material 62 may be referred to as a second conductive material which is directly adjacent the conductive core material, and the conductive material 46 may referred to as a third conductive material which is directly adjacent the second conductive material. Alternatively, the conductive material 46 may be referred to as a first conductive material and the conductive material 62 may referred to as a second conductive material. In some embodiments, the conductive material 46 may be considered to be a first conductive material having a first outer surface 61, and the material 62 may be considered to be a second conductive material which is formed adjacent to the first outer surface 61. The second conductive material 62 may be considered to comprise a second outer surface 63, and the conductive core material may be considered to be formed adjacent such second outer surface.

Figure 18:
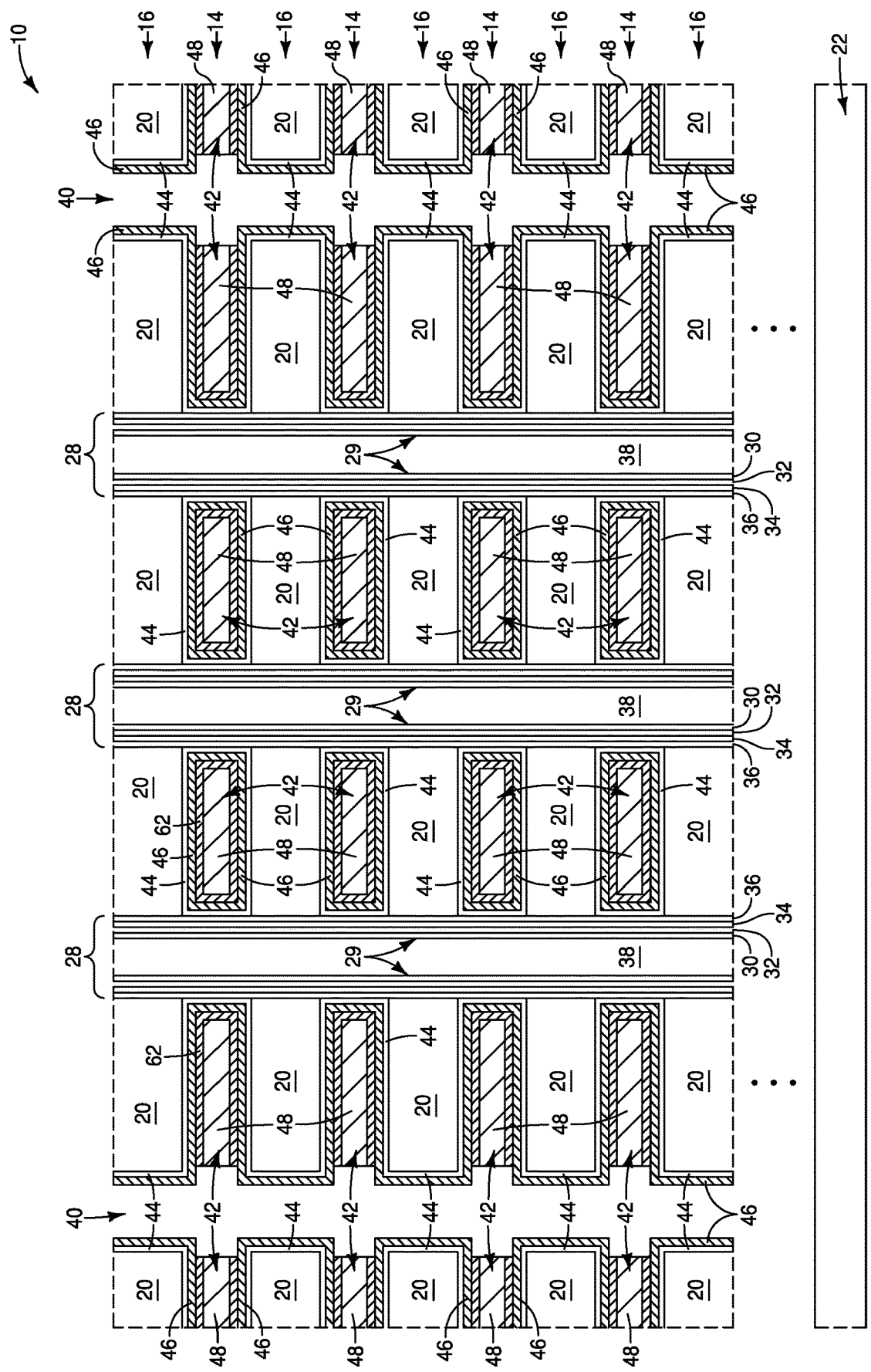

Referring to FIG. 18, the conductive materials 48 and 62 are recessed within the voids 42 in locations adjacent the slits 40 utilizing a first etch. Such recessing may utilize the same processing described above relative to FIG. 10 (e.g., a wet etch), and may utilize etching which is selective for materials 48 and 62 relative to the ruthenium-containing material 46.

Figure 19:
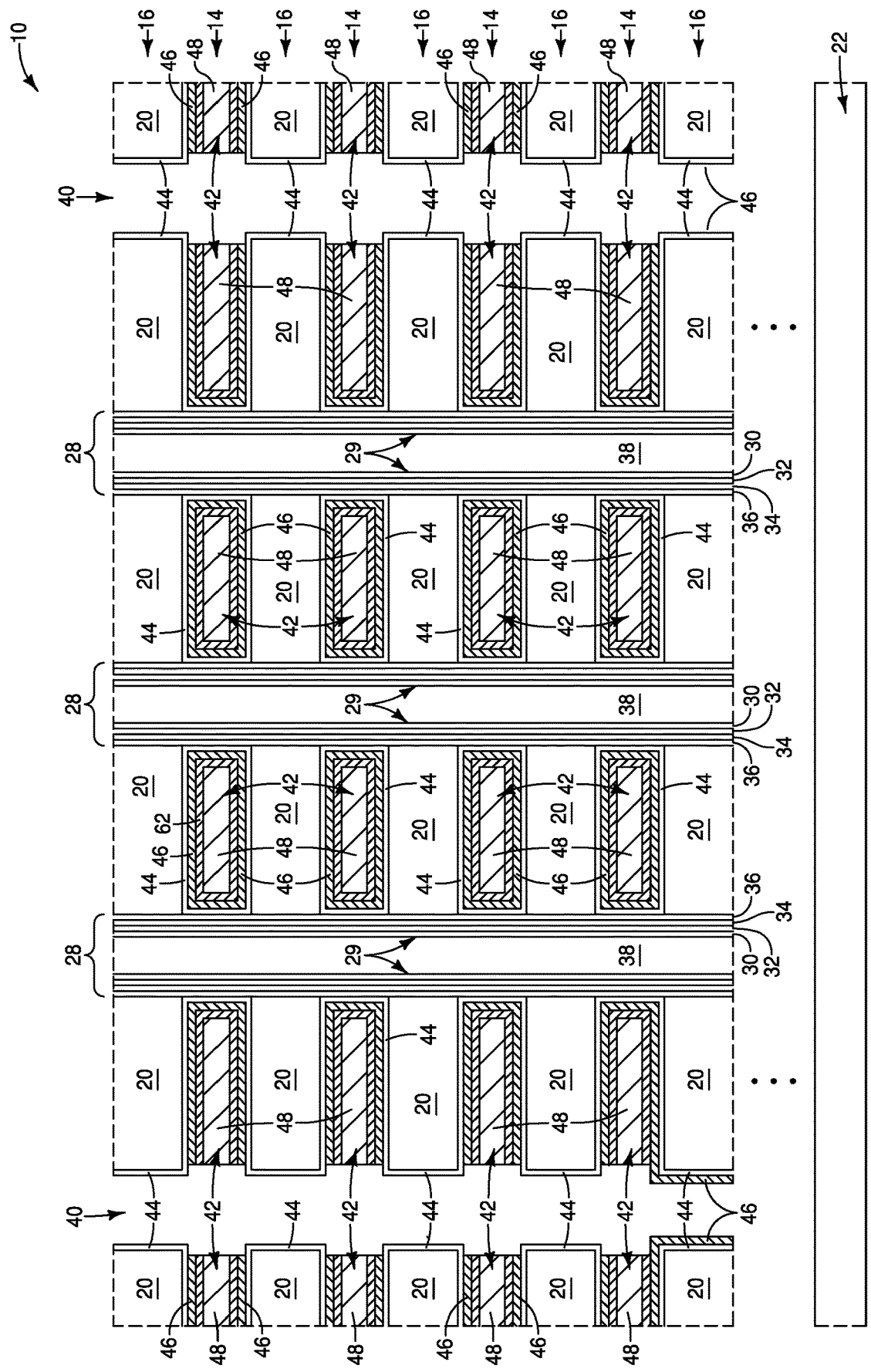

Referring to FIG. 19, the ruthenium-containing material 46 is recessed with a second etch analogous to that described above with reference to FIG. 11 (e.g., an oxidative plasma etch).

Figure 20:
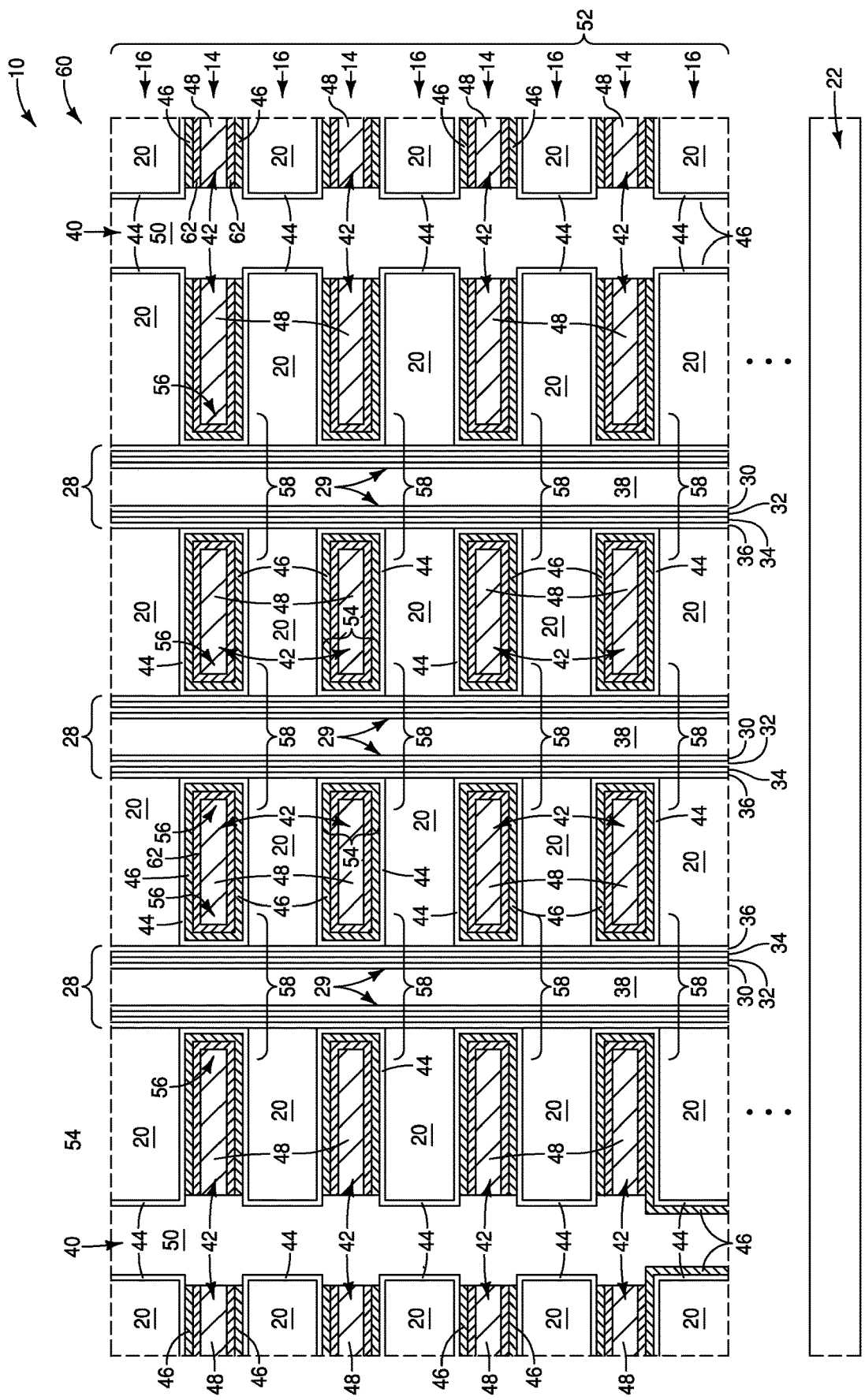

Referring to FIG. 20, the insulative material 50 is formed within the slits 40.

The assembly 10 of FIG. 20 includes the stack 52 of alternating conductive wordline levels 14 and insulative levels 16. The conductive wordline levels 14 comprise conductive wordline material (conductive gate material) 54 which comprises the three conductive materials 46, 48 and 62; with the material 46 being a ruthenium-containing material.

The conductive wordline levels 14 are incorporated into a NAND memory array 60 analogous to that described above with reference to FIG. 12. The memory array includes a plurality of memory cells 58. Regions of the conductive material 54 form gates 56 of the memory cells.

The assemblies and structures discussed above may be utilized within integrated circuits (with the term "integrated circuit" meaning an electronic circuit supported by a semiconductor substrate); and may be incorporated into electronic systems. Such electronic systems may be used in, for example, memory modules, device drivers, power modules, communication modems, processor modules, and application-specific modules, and may include multilayer, multi-chip modules. The electronic systems may be any of a broad range of systems, such as, for example, cameras, wireless devices, displays, chip sets, set top boxes, games, lighting, vehicles, clocks, televisions, cell phones, personal computers, automobiles, industrial control systems, aircraft, etc.

Unless specified otherwise, the various materials, substances, compositions, etc. described herein may be formed with any suitable methodologies, either now known or yet to be developed, including, for example, atomic layer deposition (ALD), chemical vapor deposition (CVD), physical vapor deposition (PVD), etc.

The terms "dielectric" and "insulative" may be utilized to describe materials having insulative electrical properties. The terms are considered synonymous in this disclosure. The utilization of the term "dielectric" in some instances, and the term "insulative" (or "electrically insulative") in other instances, may be to provide language variation within this disclosure to simplify antecedent basis within the claims that follow, and is not utilized to indicate any significant chemical or electrical differences.

The particular orientation of the various embodiments in the drawings is for illustrative purposes only, and the embodiments may be rotated relative to the shown orientations in some applications. The descriptions provided herein, and the claims that follow, pertain to any structures that have the described relationships between various features, regardless of whether the structures are in the particular orientation of the drawings, or are rotated relative to such orientation.

The cross-sectional views of the accompanying illustrations only show features within the planes of the cross-sections, and do not show materials behind the planes of the cross-sections, unless indicated otherwise, in order to simplify the drawings.

When a structure is referred to above as being "on", "adjacent" or "against" another structure, it can be directly on the other structure or intervening structures may also be present. In contrast, when a structure is referred to as being "directly on", "directly adjacent" or "directly against" another structure, there are no intervening structures present. The terms "directly under", "directly over", etc., do not indicate direct physical contact (unless expressly stated otherwise), but instead indicate upright alignment.

Structures (e.g., layers, materials, etc.) may be referred to as "extending vertically" to indicate that the structures generally extend upwardly from an underlying base (e.g., substrate). The vertically-extending structures may extend substantially orthogonally relative to an upper surface of the base, or not.

Some embodiments include a memory cell having a conductive gate comprising ruthenium. A charge-blocking region is adjacent the conductive gate, a charge-storage region is adjacent the charge-blocking region, a tunneling material is adjacent the charge-storage region, and a channel material is adjacent the tunneling material.

Some embodiments include an assembly having a vertical stack of alternating insulative levels and wordline levels. The wordline levels contain conductive wordline material which includes ruthenium. Semiconductor material extends through the stack as a channel structure. Charge-storage regions are between the conductive wordline material and the channel structure. Charge-blocking regions are between the charge-storage regions and the conductive wordline material.

Some embodiments include a method of forming an integrated assembly. A stack is formed to comprise alternating first and second materials. The second material is an insulative material. Channel-material-pillars are formed to extend through the stack. The first material is removed to leave voids. Conductive gate material is formed within the voids. The conductive gate material comprises ruthenium.

In compliance with the statute, the subject matter disclosed herein has been described in language more or less specific as to structural and methodical features. It is to be understood, however, that the claims are not limited to the specific features shown and described, since the means herein disclosed comprise example embodiments. The claims are thus to be afforded full scope as literally worded, and to be appropriately interpreted in accordance with the doctrine of equivalents.

I claim:

1. A method of forming an integrated assembly, comprising:
    forming a stack comprising alternating first and second materials; the second material being an insulative material;
    forming channel-material-pillars to extend through the stack;
    removing the first material to leave voids;
    forming conductive gate material within the voids; the conductive gate material comprising ruthenium; and
    recessing the conductive gate material comprising ruthenium within the voids.

2. The method of claim 1 wherein the channel-material-pillars are hollow configurations.

3. The method of claim 1 further comprising:
    forming tunneling material adjacent the channel material of the channel-material-pillars;
    forming charge-storage material adjacent the tunneling material;
    forming charge-blocking material adjacent the charge-storage material; and
    forming the conductive gate material to be on an opposing side of the charge-blocking material relative to the charge-storage material.

4. The method of claim 3 wherein the charge-storage material comprises silicon nitride.

5. The method of claim 3 further comprising:
    forming dielectric blocking material to line the voids; and
    forming the conductive gate material within the lined voids.

6. The method of claim 5 the conductive gate material consists of the ruthenium.

7. The method of claim 1 wherein the forming of the conductive gate material comprises:
    forming a liner material within the voids to line the voids, the liner material comprising the ruthenium; and
    forming a conductive core material within the lined voids, the conductive core material comprising one or more metals other than the ruthenium.

8. The method of claim 7 wherein the conductive core material consists of one or both of tungsten and molybdenum.

9. The method of claim 7 wherein the conductive core material is recessed within the voids with a first etch, and subsequently the liner is recessed within the voids with a second etch different from the first etch.

10. The method of claim 9 wherein the second etch utilizes an oxidative plasma.

11. The method of claim 1 wherein the forming of the conductive gate material comprises:
    forming a first conductive material within the voids, the first conductive material having a first outer surface, the first conductive material comprising the ruthenium;
    forming a second conductive material adjacent the outer surface of the first conductive material and within the voids, the second conductive material having a second outer surface, the second conductive material comprising one or both of titanium and tungsten; and
    forming a conductive core material adjacent the second outer surface and within the voids, the conductive core material comprising one or more metals other than the ruthenium.

12. The method of claim 11 wherein:
    the conductive core material consists of one or both of tungsten and molybdenum;
    the second conductive material comprises one or both of anium nitride and tungsten nitride; and
    the first conductive material consists of the ruthenium.

13. The method of claim 11 wherein the conductive core material and the second conductive material are recessed within the voids with a first etch, and subsequently the first conductive material is recessed within the voids with a second etch different from the first etch.

14. The method of claim 13 wherein the second etch utilizes an oxidative plasma.

15. The method of claim 1 further comprising forming a dielectric barrier liner in the voids.

16. The method of claim 15 wherein the dielectric barrier liner comprises one of more of zirconium oxide, hafnium silicate, zirconium silicate, titanium oxide, gadolinium oxide, niobium oxide and tantalum oxide.

17. The method of claim 15 wherein the dielectric barrier material comprises one of more of zirconium oxide, hafnium silicate, zirconium silicate, titanium oxide, gadolinium oxide, niobium oxide and tantalum oxide.

18. A method of forming an integrated assembly, comprising:
    forming a stack comprising alternating first and second materials; the second material being an insulative material;
    forming channel-material-pillars to extend through the stack;
    removing the first material to leave voids;
    forming conductive gate material comprising ruthenium filling the voids; and
    recessing the conductive gate material within the voids.

19. The method of claim 18 further comprising forming dielectric barrier material as a liner in the void against the conductive gate material.

20. The method of claim 19 wherein the dielectric barrier material comprises one of more of zirconium oxide, hafnium silicate, zirconium silicate, titanium oxide, gadolinium oxide, niobium oxide and tantalum oxide.

21. The method of claim 18 further comprising a second recessing of the conductive gate material with a first etch different from a second etch.

22. A method of forming an integrated assembly, comprising:
    forming a stack comprising alternating first and second materials; the second material being an insulative material;
    forming channel-material-pillars to extend through the stack;
    removing the first material to leave voids;
    forming a first liner in the void comprising ruthenium material, the first liner comprising an inner periphery exposed in the void; and
    forming a second liner against the inner periphery of the first liner.

23. The method of claim 22 wherein the second liner comprises a conductive material.

24. The method of claim 22 wherein the second liner comprises one or more of metal nitrides.

25. The method of claim 22 wherein the second liner comprises one or more of titanium nitride and tungsten nitride.

26. The method of claim 22 further comprising a third liner in the voids.

27. The method of claim 26 wherein the third liner comprises dielectric barrier material.

28. The method of claim 26 wherein the third liner is between the insulative material and the first liner.

* * * * *